(12) United States Patent
DiCicco et al.

(10) Patent No.: US 12,082,792 B2
(45) Date of Patent: Sep. 10, 2024

(54) SYSTEMS AND METHODS FOR CREATING A PUNCTURE BETWEEN AORTA AND THE LEFT ATRIUM

(71) Applicant: Boston Scientific Medical Device Limited, Ballybrit (IE)

(72) Inventors: Matthew DiCicco, Guelph (CA); John Paul Urbanski, Toronto (CA)

(73) Assignee: Boston Scientific Medical Device Limited, Ballybrit (IE)

(*) Notice: Subject to any disclaimer, the term of this patent is extended or adjusted under 35 U.S.C. 154(b) by 675 days.

(21) Appl. No.: 17/184,729

(22) Filed: Feb. 25, 2021

(65) Prior Publication Data

US 2021/0259671 A1    Aug. 26, 2021

Related U.S. Application Data

(60) Provisional application No. 62/981,454, filed on Feb. 25, 2020.

(51) Int. Cl.
*A61B 17/00* (2006.01)
*A61B 17/32* (2006.01)
(Continued)

(52) U.S. Cl.
CPC .......... *A61B 17/00234* (2013.01); *A61B 17/320016* (2013.01); *A61B 18/1492* (2013.01);
(Continued)

(58) Field of Classification Search
CPC .......... A61B 2017/00252; A61B 2017/00247; A61B 2017/00358; A61B 2018/00601;
(Continued)

(56) References Cited

U.S. PATENT DOCUMENTS 175,254 A    3/1876  Oberly
827,626 A    7/1906  Gillet
(Continued)

FOREIGN PATENT DOCUMENTS

EP    2550988    1/2013
EP    3064246    9/2016
(Continued)

*Primary Examiner* — Linda C Dvorak
*Assistant Examiner* — Davina E. Lee
(74) *Attorney, Agent, or Firm* — Nelson Mullins Riley & Scarborough LLP

(57) ABSTRACT

A method of puncturing from an aorta into a left atrium using a puncturing device. The method involves a step of accessing a carotid artery and advancing a puncturing device through the carotid artery into an aorta. Advancing a sheath and a dilator over the puncturing device through the carotid artery and into the aorta such that a puncturing tip of the puncturing device is aligned with a distal tip of the sheath and a distal tip of the dilator, forming a puncturing assembly. Positioning the puncturing assembly at a target site within the aorta to gain access to a left atrium of a heart. Tenting a tissue between the aorta and the left atrium using the puncturing assembly. Creating a puncture through the tissue by advancing the puncturing device such that a channel between the aorta and the left atrium is formed.

20 Claims, 18 Drawing Sheets

(51) Int. Cl.
- *A61B 18/14* (2006.01)
- *A61B 5/367* (2021.01)
- *A61B 8/08* (2006.01)
- *A61B 18/00* (2006.01)
- *A61B 90/00* (2016.01)
- *A61M 5/00* (2006.01)
- *A61M 25/09* (2006.01)

(52) U.S. Cl.
CPC ............ *A61B 5/367* (2021.01); *A61B 8/0883* (2013.01); *A61B 2017/00252* (2013.01); *A61B 2017/00358* (2013.01); *A61B 2017/00991* (2013.01); *A61B 2018/00357* (2013.01); *A61B 2018/00601* (2013.01); *A61B 2090/064* (2016.02); *A61B 2090/376* (2016.02); *A61M 5/007* (2013.01); *A61M 25/09* (2013.01)

(58) Field of Classification Search
CPC . A61B 5/367; A61B 17/11; A61B 2017/1107; A61M 25/09
See application file for complete search history.

(56) References Cited

U.S. PATENT DOCUMENTS

| | | | |
|---|---|---|---|
| 848,711 | A | 4/1907 | Weaver |
| 1,072,954 | A | 9/1913 | Junn |
| 1,279,654 | A | 9/1918 | Charlesworth |
| 1,918,094 | A | 7/1933 | Geekas |
| 1,996,986 | A | 4/1935 | Weinberg |
| 2,021,989 | A | 11/1935 | De Master |
| 2,146,636 | A | 2/1939 | Lipchow |
| 3,429,574 | A | 2/1969 | Williams |
| 3,448,739 | A | 6/1969 | Stark et al. |
| 3,575,415 | A | 4/1971 | Fulp et al. |
| 3,595,239 | A | 7/1971 | Petersen |
| 4,129,129 | A | 12/1978 | Amrine |
| 4,244,362 | A | 1/1981 | Anderson |
| 4,401,124 | A | 8/1983 | Guess et al. |
| 4,639,252 | A | 1/1987 | Kelly et al. |
| 4,641,649 | A | 2/1987 | Walinsky et al. |
| 4,669,467 | A | 6/1987 | Willett et al. |
| 4,682,596 | A | 7/1987 | Bales et al. |
| 4,790,311 | A | 12/1988 | Ruiz |
| 4,790,809 | A | 12/1988 | Kuntz |
| 4,793,350 | A | 12/1988 | Mar et al. |
| 4,807,620 | A | 2/1989 | Strul et al. |
| 4,832,048 | A | 5/1989 | Cohen |
| 4,840,622 | A | 6/1989 | Hardy |
| 4,863,441 | A | 9/1989 | Lindsay et al. |
| 4,884,567 | A | 12/1989 | Elliott et al. |
| 4,892,104 | A | 1/1990 | Ito et al. |
| 4,896,671 | A | 1/1990 | Cunningham et al. |
| 4,928,693 | A | 5/1990 | Goodin et al. |
| 4,936,281 | A | 6/1990 | Stasz |
| 4,960,410 | A | 10/1990 | Pinchuk |
| 4,977,897 | A | 12/1990 | Hurwitz |
| 4,998,933 | A | 3/1991 | Eggers et al. |
| 5,006,119 | A | 4/1991 | Acker et al. |
| 5,019,076 | A | 5/1991 | Yamanashi et al. |
| 5,047,026 | A | 9/1991 | Rydell |
| 5,081,997 | A | 1/1992 | Bosley et al. |
| 5,098,392 | A | 3/1992 | Fleischhacker et al. |
| 5,098,431 | A | 3/1992 | Rydell |
| 5,112,048 | A | 5/1992 | Kienle |
| 5,154,724 | A | 10/1992 | Andrews |
| 5,201,756 | A | 4/1993 | Horzewski et al. |
| 5,209,741 | A | 5/1993 | Spaeth |
| 5,211,183 | A | 5/1993 | Wilson |
| 5,221,256 | A | 6/1993 | Mahurkar |
| 5,230,349 | A | 7/1993 | Langberg |
| 5,281,216 | A | 1/1994 | Klicek |
| 5,300,068 | A | 4/1994 | Rosar et al. |
| 5,300,069 | A | 4/1994 | Hunsberger et al. |
| 5,312,341 | A | 5/1994 | Turi |
| 5,314,418 | A | 5/1994 | Takano et al. |
| 5,318,525 | A | 6/1994 | West et al. |
| 5,327,905 | A | 7/1994 | Avitall |
| 5,364,393 | A | 11/1994 | Auth et al. |
| 5,372,596 | A | 12/1994 | Klicek et al. |
| 5,380,304 | A | 1/1995 | Parker |
| 5,395,341 | A | 3/1995 | Slater |
| 5,397,304 | A | 3/1995 | Truckai |
| 5,403,338 | A | 4/1995 | Milo |
| 5,423,809 | A | 6/1995 | Klicek |
| 5,425,382 | A | 6/1995 | Golden et al. |
| 5,490,859 | A | 2/1996 | Mische et al. |
| 5,497,774 | A | 3/1996 | Swartz et al. |
| 5,499,975 | A | 3/1996 | Cope et al. |
| 5,507,751 | A | 4/1996 | Goode et al. |
| 5,509,411 | A | 4/1996 | Littmann et al. |
| 5,540,681 | A | 7/1996 | Strul et al. |
| 5,545,200 | A | 8/1996 | West et al. |
| 5,555,618 | A | 9/1996 | Winkler |
| 5,571,088 | A | 11/1996 | Lennox et al. |
| 5,575,766 | A | 11/1996 | Swartz et al. |
| 5,575,772 | A | 11/1996 | Lennox |
| 5,599,347 | A | 2/1997 | Hart et al. |
| 5,605,162 | A | 2/1997 | Mirzaee et al. |
| 5,617,878 | A | 4/1997 | Taheri |
| 5,622,169 | A | 4/1997 | Golden et al. |
| 5,624,430 | A | 4/1997 | Eton et al. |
| 5,667,488 | A | 9/1997 | Lundquist et al. |
| 5,673,695 | A | 10/1997 | McGee et al. |
| 5,674,208 | A | 10/1997 | Berg et al. |
| 5,683,366 | A | 11/1997 | Eggers et al. |
| 5,720,744 | A | 2/1998 | Eggleston et al. |
| 5,741,249 | A | 4/1998 | Moss et al. |
| 5,766,135 | A | 6/1998 | Terwilliger |
| 5,779,688 | A | 7/1998 | Imran et al. |
| 5,810,764 | A | 9/1998 | Eggers et al. |
| 5,814,028 | A | 9/1998 | Swartz et al. |
| 5,830,214 | A | 11/1998 | Flom et al. |
| 5,836,875 | A | 11/1998 | Webster, Jr. |
| 5,849,011 | A | 12/1998 | Jones et al. |
| 5,851,210 | A | 12/1998 | Torossian |
| 5,885,227 | A | 3/1999 | Finlayson |
| 5,888,201 | A | 3/1999 | Stinson et al. |
| 5,893,848 | A | 4/1999 | Negus et al. |
| 5,893,885 | A | 4/1999 | Webster, Jr. |
| 5,904,679 | A | 5/1999 | Clayman |
| 5,916,210 | A | 6/1999 | Winston |
| 5,921,957 | A | 7/1999 | Killion et al. |
| 5,931,818 | A | 8/1999 | Werp et al. |
| 5,944,023 | A | 8/1999 | Johnson et al. |
| 5,951,482 | A | 9/1999 | Winston et al. |
| 5,957,842 | A | 9/1999 | Littmann et al. |
| 5,964,757 | A | 10/1999 | Ponzi |
| 5,967,976 | A | 10/1999 | Larsen et al. |
| 5,989,276 | A | 11/1999 | Houser et al. |
| 6,007,555 | A | 12/1999 | Devine |
| 6,009,877 | A | 1/2000 | Edwards |
| 6,013,072 | A | 1/2000 | Winston et al. |
| 6,017,340 | A | 1/2000 | Cassidy et al. |
| 6,018,676 | A | 1/2000 | Davis et al. |
| 6,030,380 | A | 2/2000 | Auth et al. |
| 6,032,674 | A | 3/2000 | Eggers et al. |
| 6,036,677 | A | 3/2000 | Javier, Jr. et al. |
| 6,048,349 | A | 4/2000 | Winston et al. |
| 6,053,870 | A | 4/2000 | Fulton, III |
| 6,053,904 | A | 4/2000 | Scribner et al. |
| 6,056,747 | A | 5/2000 | Saadat et al. |
| 6,063,093 | A | 5/2000 | Winston et al. |
| 6,093,185 | A | 7/2000 | Ellis et al. |
| 6,106,515 | A | 8/2000 | Winston et al. |
| 6,106,520 | A | 8/2000 | Laufer et al. |
| 6,117,131 | A | 9/2000 | Taylor |
| 6,142,992 | A | 11/2000 | Cheng et al. |
| 6,146,380 | A | 11/2000 | Racz et al. |
| 6,155,264 | A | 12/2000 | Ressemann et al. |
| 6,156,031 | A | 12/2000 | Aita et al. |
| 6,171,305 | B1 | 1/2001 | Sherman |
| 6,179,824 | B1 | 1/2001 | Eggers et al. |

(56) References Cited

U.S. PATENT DOCUMENTS

| | | |
|---|---|---|
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,270,476 B1 | 8/2001 | Santoianni |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,048,733 B2 | 5/2006 | Hartley et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 * | 2/2010 | Chanduszko ...... A61B 17/3468 |
| | | 128/898 |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,337,518 B2 * | 12/2012 | Nance ................ A61B 17/3478 |
| | | 606/194 |
| 8,388,549 B2 | 3/2013 | Paul et al. |
| 8,500,697 B2 | 3/2013 | Kurth et al. |
| 9,072,872 B2 | 7/2015 | Asleson et al. |
| 9,757,541 B2 | 9/2017 | Haarer |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2001/0044591 A1 | 11/2001 | Stevens et al. |
| 2001/0051790 A1 | 12/2001 | Parker |
| 2002/0019644 A1 | 2/2002 | Hastings et al. |
| 2002/0022781 A1 | 2/2002 | McIntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123698 A1 * | 9/2002 | Garibotto .......... A61B 17/3417 |
| | | 600/585 |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0208220 A1 | 11/2003 | Worley et al. |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |

(56) References Cited

U.S. PATENT DOCUMENTS

| | | |
|---|---|---|
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0185522 A1 | 8/2007 | Davies et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0243081 A1 | 10/2008 | Nance et al. |
| 2008/0243222 A1 | 10/2008 | Schafersman et al. |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0022948 A1 | 1/2010 | Wilson et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2010/0249908 A1 | 11/2010 | Chau et al. |
| 2011/0046619 A1 | 2/2011 | Ducharme |
| 2011/0087261 A1 | 4/2011 | Wittkampf |
| 2011/0130752 A1 | 6/2011 | Ollivier |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0109079 A1 | 5/2012 | Asleson |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2015/0148731 A1* | 5/2015 | Mcnamara ......... A61B 17/0057 604/9 |
| 2015/0157353 A1 | 6/2015 | Lenker et al. |
| 2015/0258312 A1* | 9/2015 | Tuseth ............ A61B 17/00234 604/8 |
| 2016/0175009 A1 | 6/2016 | Davies |
| 2016/0220741 A1 | 8/2016 | Garrison et al. |
| 2017/0189063 A1* | 7/2017 | Tuseth ................ A61M 60/178 |
| 2018/0098847 A1* | 4/2018 | Tuseth ................ A61M 60/148 |
| 2019/0021763 A1 | 1/2019 | Zhou et al. |
| 2019/0247035 A1 | 8/2019 | Gittard et al. |

FOREIGN PATENT DOCUMENTS

| | | | |
|---|---|---|---|
| JP | 2007510458 | 4/2007 | |
| JP | 2009537255 | 10/2009 | |
| JP | 2010227580 | 10/2010 | |
| JP | 2011206179 | 10/2011 | |
| WO | WO-0170133 A2 * | 9/2001 | ......... A61B 17/3207 |
| WO | 2005065562 | 7/2005 | |
| WO | 2008066557 | 6/2008 | |
| WO | 2008079828 | 7/2008 | |
| WO | WO-2010132451 A2 * | 11/2010 | .............. A61M 1/10 |
| WO | 2011014496 | 2/2011 | |
| WO | 2013101632 | 7/2013 | |
| WO | 2014182969 | 11/2014 | |
| WO | WO-2020232384 A1 * | 11/2020 | .............. A61B 17/11 |

* cited by examiner

SYSTEMS AND METHODS FOR CREATING A PUNCTURE BETWEEN AORTA AND THE LEFT ATRIUM

TECHNICAL FIELD

The disclosure relates to systems and methods for creating a puncture in tissue. More specifically, the disclosure relates to a method and device to create a puncture (or a shunt) from the aorta to left atrium for communication between the aorta and left atrium.

BACKGROUND OF THE ART

It is often required to create perforations between various chambers of the heart and surrounding central vasculature to study etiology, pressure gradients, or enable end-therapies. One such therapy may include implanting a left ventricular assist device (LVAD) to help heart failure patients by providing sufficient blood flow to peripheral organs, keeping patients alive as a bridge to transplantation or engendering return of native heart function. Traditionally, LVAD catheters are tracked from the left atrium, through the mitral valve, to the left ventricle, through the aortic valve, and to the aorta. This process may lead to complications such as effusions, valve stenosis, hematoma, and/or vessel dissections. With recent advances in the structural heart field and new heart failure devices, there has been a transition to less invasive methods of implantation of traditional LVADs; specifically, around the new percutaneous LVAD pump devices as they are non-invasive to the ventricular muscle. Percutaneous LVAD pump devices require support from a percutaneous catheter through a passageway or connection between the left atrium to the aorta, where a shunt may be inserted. A shunt is a hole or small passage which allows the movement of blood from the left atrium to the aorta. Creating a direct fluid communication pathway (i.e., via a shunt) between the left atrium and aorta is significant as the end-therapy device, approach, and selected tools used to create the communication play a role in optimal site-selection.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1A:
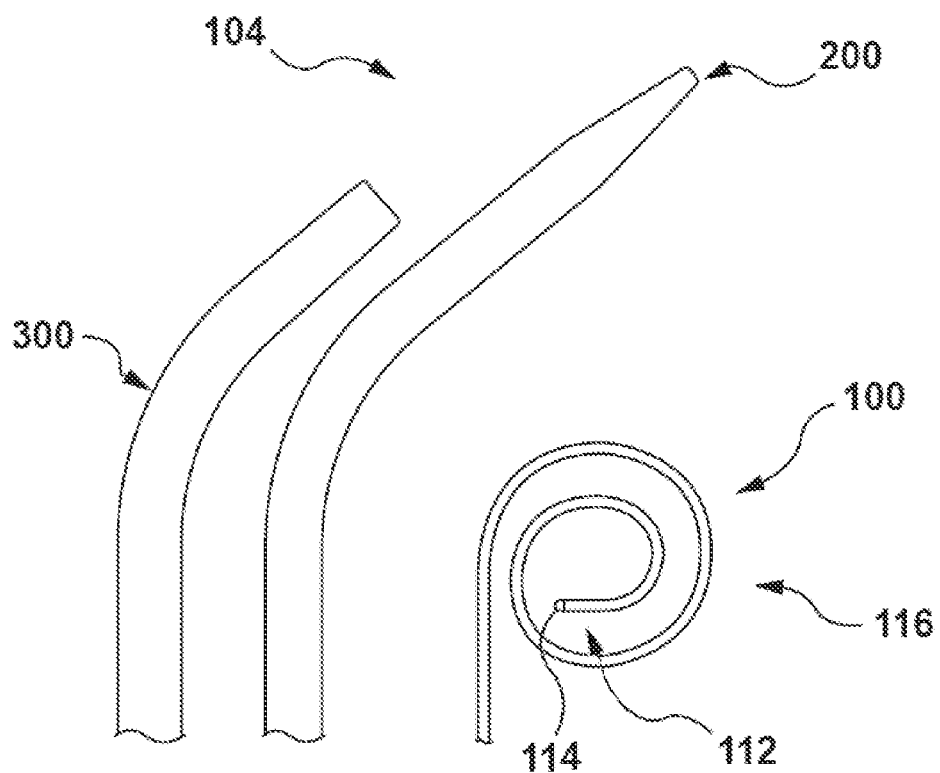
FIG. 1A-1B are illustrations of an assemblies that incorporate various devices to be used for puncturing a target tissue in accordance with an embodiment of the present invention.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The creation of a connection (i.e., fluid communication) between the left atrium and the aorta may be approached through arterial vasculature from a superior arterial vasculature approach. There are additional benefits of a superior approach to the target site which include, length management of associated toolsets of any end-therapy device, less tortuous path to potential optimal access sites, and ideal force transmission for dilation and placement of any end-therapy devices.

Thus, there exists a need to provide physicians with a method of puncturing the tissue between the left atrium and the aorta to create a connection, gap, or hole for fluid communication.

In accordance with some embodiments, details of the devices are disclosed in application number PCT/IB2013/060287 and publication number WO2015019132, and in application number PCT/IB2017/056777 and publication number WO2018083599, which are incorporated herein by reference in its entirety.

The Assembly and Puncturing Device

In an embodiment, an assembly is provided for puncturing tissue, where the assembly comprises a puncturing device for puncturing tissue. The puncturing device preferably comprises an atraumatic tip. In the preferred embodiment, the atraumatic tip comprises an energy delivery device such as an electrode, capable of delivering radiofrequency energy to the target tissue, thereby creating a puncture in the tissue. In some embodiments, the puncturing device may be flexible, allowing the flexible puncturing device to also be used as an exchange or guidewire. In alternative embodiments, the flexible puncturing device may comprise a sharp distal tip which enables the user to mechanically puncture the tissue. In further alternative embodiments, the puncturing device may be a steerable needle or a steerable power catheter.

The assembly additionally comprises ancillary devices, such as a sheath and/or dilator, for supporting the puncturing device. The sheath and/or dilator are operable to be selectively usable with the flexible puncturing device. In some embodiments, the flexible puncturing device is an energy-based device for delivering energy to the tip of the puncturing device in order to puncture the septum. In some embodiments, the flexible puncturing device has a lumen and one or more apertures. The lumen and aperture may combine to form a pressure transmitting lumen. The flexible puncturing device may be operable to be coupled to a pressure sensing mechanism, such as a pressure sensor, to measure the pressure transmitted through the lumen. In some embodiments, fluid (such as imaging or contrast fluid) is injected through the lumen and one or more apertures.

The assembly enables the flexible puncturing device to be usable independently from the ancillary devices as an exchange or guidewire during a portion of the procedure and to be usable in co-operation with other devices for puncturing tissue during another portion of the procedure. This reduces the number of exchanges needed by allowing the flexible puncture device to be used for puncturing tissue, and as an exchange wire. The ancillary devices facilitate positioning of the energy delivery portion of the flexible puncturing device against the desired target tissue location and may additionally reduce procedure complexity and enhance procedural efficiency.

Figure 1B:
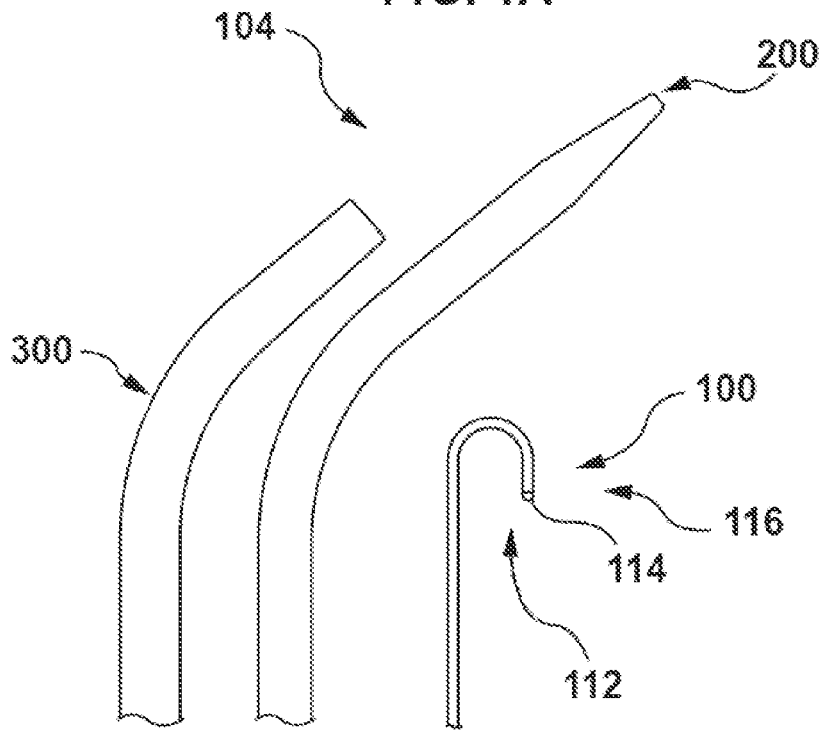

FIGS. 1A and 1B are an illustrations of an assembly 104 that incorporates embodiments of devices that may be utilized during the course of the procedure as described further hereinbelow. The assembly 104 is used for puncturing tissue, such as for creating a puncture between the aorta and the left atrium to provide fluid communication between the two. The assembly 104 comprises a tissue puncturing device 100 and ancillary devices. In this embodiment, the ancillary devices comprise a sheath 300 and a dilator 200 that are selectively usable with the puncture device 100. As described previously, the puncture device 100 may be substantially flexible, enabling it to be used as an exchange wire or guidewire. In this embodiment, the flexible puncture device 100, dilator 200, and sheath 300, enhance procedural efficiency by facilitating exchange and positioning. In some embodiments, the flexible puncture device 100 comprises an energy delivery device 114 that is operable to deliver energy in order to puncture tissue. In an alternative embodiment, the flexible puncturing device 100 may comprise a sharp distal tip, which may be used to mechanically puncture tissue. In another embodiment, the puncturing device may utilize the "bovie" method to perform the puncture the tissue.

In specific examples, the distal portions 116 of assembly 104 comprise a pigtail or J-tip configuration, as shown in FIGS. 1A and 1B respectively. These configurations facilitate anchoring of the puncture device 100, for example after puncture. The puncture device 100 comprises a substantially atraumatic distal tip 112. The distal tip 112 may further comprise an energy delivery device 114, such as an electrode, capable of delivering radiofrequency energy in order to puncture tissue. In a specific instance of this example, the puncture device 100 comprises a flexible radiofrequency wire that has a distal electrode tip 114 for delivering radiofrequency in order to puncture tissue. In some instances, the radiofrequency wire is a flexible wire which is generally electrically insulated save for selected distal regions such as the distal electrode tip 114. In an alternative embodiment, the puncture device 100 may comprise a sharp distal tip relies on the application of mechanical force to puncture the tissue. In another embodiment, the puncture device 100 may be a steerable needle or a steerable power catheter. A preferred feature of the puncture device 100 is to have sufficient flexibility such that it can be maneuvered to the desired target location.

FIGS. 1A and 1B illustrate embodiments of a substantially flexible energy based puncturing device such as a radiofrequency (RF) wire that is sufficiently flexible to enable access to the left atrium via the aorta. An active tip 114 at the distal end 112 is operable to deliver energy for puncturing tissue such as the aorta to create a puncture site through to the left atrium, which the RF wire can be advanced, for example to enter the left atrium. In a specific embodiment the RF wire has an outer diameter (OD) of 0.035" and a wire length of 180 cm. In another example. The RF wire has an outer diameter (OD) of 0.032". In a further example, the RF wire has a radiopaque marker.

FIG. 1A shows a specific embodiment of a pigtail RF wire where the distal section 116 is biased to form a coil for anchoring the RF wire beyond the puncture site. FIG. 1B shows a specific embodiment of a J-tip RF wire where the distal section 116 substantially forms a "J". Typically, when distal section 116 is advanced out of a dilator and beyond the septum, the biased curves act as an anchor in the left atrium, providing a rail into the left atrium. In an alternative embodiment, the distal portion of the RF wire may comprise an anchoring element which would help anchor the RF wire at a desired location.

In some embodiments of the assembly 104, as shown in FIGS. 1A and 1B, comprises a dilator 200 and a sheath 300. The dilator 200 and sheath 300 each define a respective lumen through which devices may be inserted. Further details of the exemplary dilator 200 and sheath 300 are discussed hereinbelow.

The Dilator

In some examples, the dilator 200 provides stiffness to the assembly 104 to facilitate force transmission to a distal end of the assembly 104. In other examples, the sheath 300 is usable with the dilator 200 to provide stiffness to the assembly 104 to enable force or torque to be transmitted to a distal end of the assembly 104. In some such examples, the sheath 300 may be coupled to the dilator 200 which enables force and/or torque transmission using one or more of the components (i.e., the sheath 300 or the dilator 200). In other words, the user may just manipulate the sheath 300 or the dilator 200 and the puncture device 100 will follow the guidance of the sheath 300 or dilator 200.

In some embodiments of the present invention, the dilator 200 may be a flexible dilator 200. The flexible dilator 200 may be used in conjunction with a sheath 300, such as a steerable sheath 300, in order to gain access to a region of tissue within a patient. The steerable sheath 300 comprises a lumen therethrough for receiving the dilator 200 and provides the user with a range of deflection angles. The dilator 200 includes a substantially flexible or soft section that provides minimal resistance to deflection and is operable to be deflected under guidance to allow the dilator 200 to reach a desired site within a region of tissue within the patient's body to facilitate advancement of the distal end region. The flexible region allows the dilator 200 to conform to the curvature of the steerable sheath 300 that is achieved through actuation of the steerable sheath 300. In some embodiments, the distal end of the dilator 200 extends beyond the distal end of the sheath 300 to improve access to the target tissue within the patient's body.

In one embodiment of the present invention, the dilator 200 comprises a rigid distal end region and a flexible intermediate region. The dilator 200 may be configured such that, when the dilator 200 is inserted into the lumen of the steerable sheath 300, the location of the flexible intermediate region corresponds to a location of a region of the steerable sheath 300 that is amenable to deflection. This region of deflection may also be referred to as a "curvature-imparting region" or an "articulating region". The dilator 200 further comprises a rigid distal end region having a rigidity greater than the flexible intermediate region to enable the dilator 200 to advance through tissue.

In the aforementioned embodiments, the dilator 200 is structured such that, during use, the flexible intermediate region of the dilator 200 is configured to provide minimal resistance to deflection. This enables the steerable sheath 300 to reach a desired deflection angle, from said range of deflection angles, to position the dilator 200 rigid distal end region at a desired location within the region of tissue. The dilator 200 rigid distal end region to facilitates advancement of the dilator 200 there-through.

Embodiments of a dilator 200 of the present invention are sufficiently flexible to allow the ancillary device to guide and position the dilator and/or additional devices in a wide array of patient anatomies. Embodiments of the dilator 200 accomplish this function by providing a flexible intermediate region having reduced stiffness. The location of the flexible region, when the dilator 200 is inserted into/through the ancillary device, corresponds to a region of the ancillary device that is amenable to deflection or has a particular shape or curve, whereby the flexibility of the dilator 200 at that location helps to ensure that the dilator 200 does not substantially impair the ability of the ancillary device to retain, maintain or reach its intended shape or curvature. In some embodiments, the dilator 200, while being sufficiently flexible along the intermediate region, has sufficient stiffness along a distal end region to allow the dilator 200 to be tracked or advanced across tissue for dilating a perforation or puncture at the desired target tissue site.

Figure 2A:
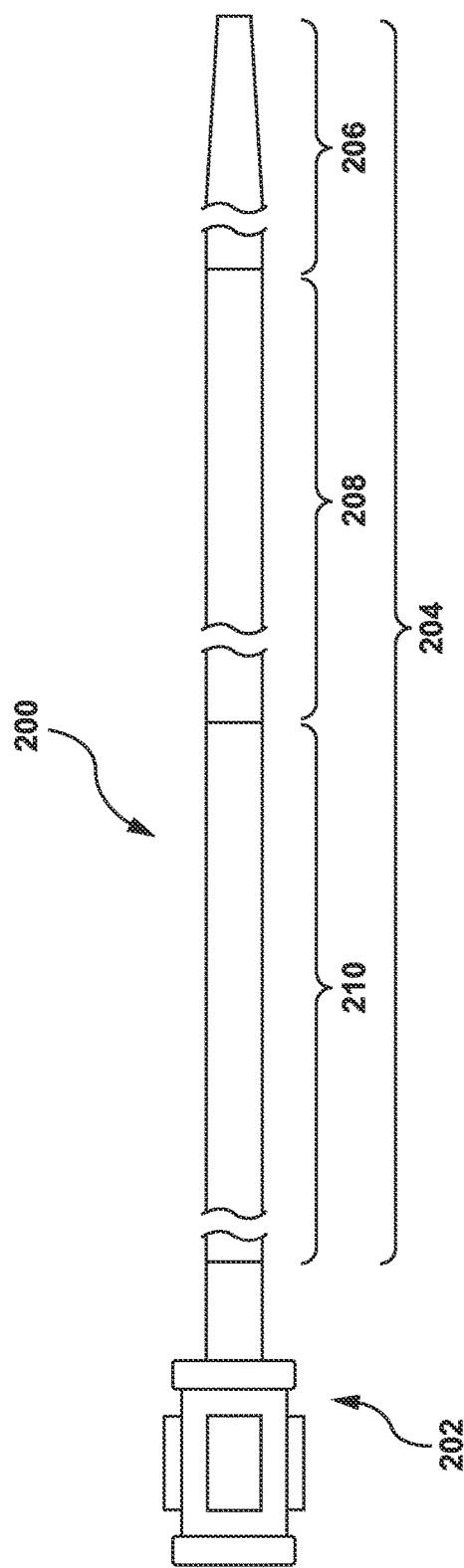
FIG. 2A is an illustration of a dilator in accordance an embodiment of the present invention.
Figure 2B:
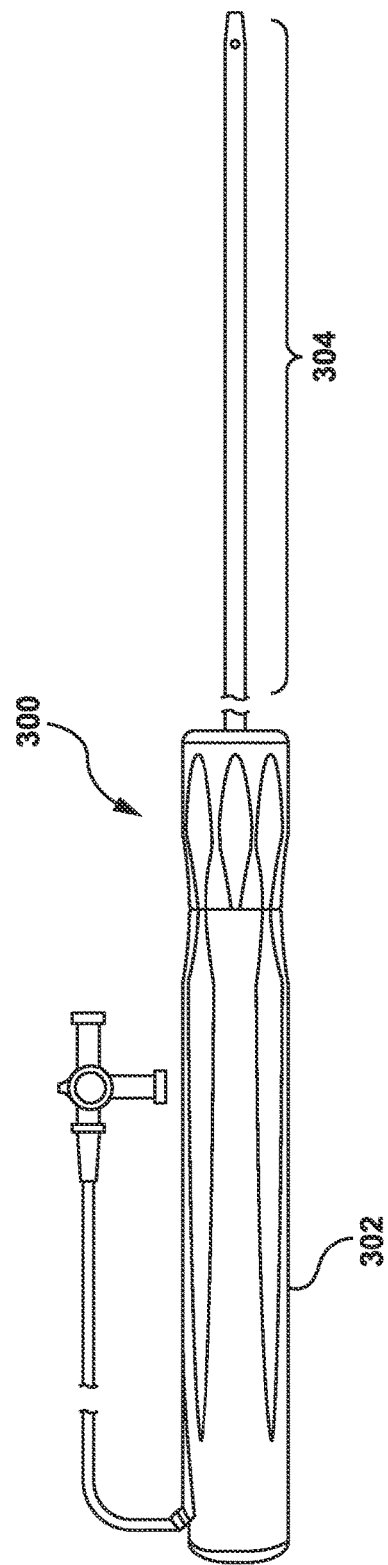
FIG. 2B is an illustration of a steerable sheath for use with a dilator in accordance with an embodiment of the present invention.

In accordance with one embodiment of the present invention, as shown in FIG. 2A, a flexible dilator 200 is disclosed for use with a steerable sheath 300 (shown in FIG. 2B) to access a region of tissue within a patient's body. The steerable sheath 300 has a range of deflection angles and can achieve a range of curvatures upon actuation. Referring again to FIG. 2A, the dilator 200 comprises a dilator hub 202 that is coupled to an elongate member 204 that comprises regions of varying flexibility including an intermediate region 208 that terminates in a distal end region 206. In accordance with an embodiment of the present invention, the intermediate region 208 is a substantially flexible or soft section that provides minimal resistance to deflection and is operable to be deflected under guidance to allow the dilator 200 to reach a desired site within a region of tissue within the patient's body to facilitate advancement of the distal end region 206 there-through. The flexible intermediate region 208 allows the dilator 200 to conform to the curvature of the steerable sheath 300 that is achieved through actuation of the steerable sheath 300. Thus, in some embodiments, as outlined herein, the flexible intermediate region 208 does not inhibit the range of motion of the steerable sheath 300.

Additionally, the elongate member 204 of the dilator 200 further comprises a distal end region 206 that is formed distally adjacent to the flexible intermediate region 208, such that the flexible intermediate region 208 continues distally until (and terminates at) a proximal boundary or edge of the distal end region 206. In other words, the distal end region 206 extends proximally from the distal edge of the dilator 200 until a distal edge of the flexible intermediate region 208. The distal end region 206 has a stiffness or rigidity that is greater than the flexible intermediate region 208 to facilitate advancement of the dilator 200 through the tissue once the dilator 200 has been positioned at the desired tissue site, such as a desired puncture site. The stiff or substantially rigid distal end region 206 provides enhanced pushability and may prevent deformation thereof during advancement of the distal end region 206 through the tissue, for example at the puncture site in order to dilate the puncture site.

As outlined previously, in accordance with an embodiment of the present invention, a dilator 200 is provided that is usable with a steerable sheath 300 to access a region of tissue within a patient's body. The steerable sheath 300 may be of the type shown in FIG. 2B, comprising an articulating portion or deflectable region 304 that is amenable to deflection upon actuation of a steerable actuation mechanism, for example such as a knob of a handle 302. During use, the dilator 200 is inserted within the steerable sheath 300 for use therewith such that the position of the flexible intermediate region 208 of the dilator 200 corresponds to the articulating portion or deflectable region 304 of the steerable sheath 300. This enables the steerable sheath 300 to reach its allowable range of curvatures or deflection upon actuation, as minimal resistance is introduced by the dilator 200. In other words, the flexible intermediate region 208 of the dilator 200 does not impart rigidity to the steerable sheath 300 as the dilator 200 is being steered by the steerable sheath 300. This enables the steerable sheath 300 to position the distal end region 206 of the dilator 200 at a desired target location within a region of tissue such as at a desired puncture location to enable the distal end region 206 to subsequently advance there-through while dilating the puncture site.

In a specific embodiment, an 8.5 French steerable sheath 300 with a 45 cm usable length and an 8.5 French dilator 200 with a usable length of 67 cm is used. The dilator 200 tapers down to an outer diameter (OD) of about 0.046" (about 1.2 mm) and an inner diameter (ID) of about 0.036" (about 0.9 mm) at the distal tip.

Figure 2C:
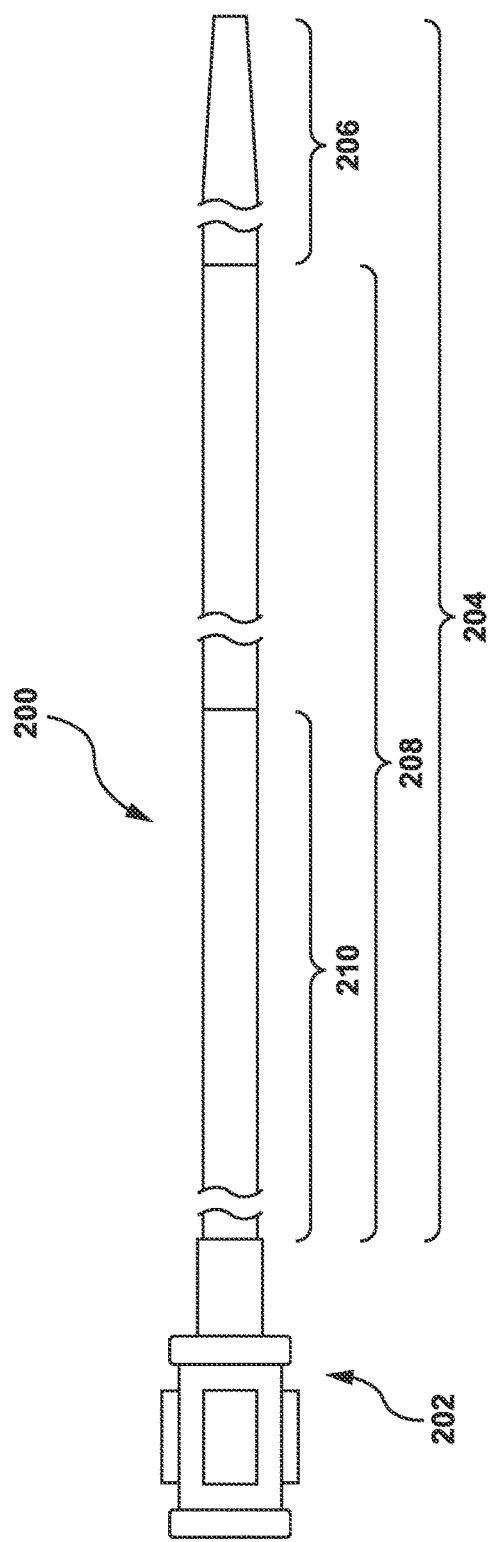
FIG. 2C is an illustration of a dilator in accordance with an alternate embodiment of the present invention.

In one embodiment, with reference to FIG. 2A, dilator 200 further comprises a proximal region 210 that forms a part of elongate member 204 of dilator 200. The proximal region 210 extends proximally from the flexible intermediate region 208. More specifically, the proximal region 210 extends proximally from a proximal boundary of the flexible intermediate region 208 and may extend until the hub 202. In some embodiments the proximal region 210 may also be formed from a flexible material and exhibits flexibility. Alternatively, in other embodiments, as shown in FIG. 2C, the flexible intermediate region 208 may extend along the proximal region 210 and may include the proximal region 210. In some such embodiments, the flexible intermediate region 208 may have varying regions of flexibility. In some embodiments, the proximal region 210 of the dilator 200 may be flexible, while in other embodiments the proximal region 210 may be stiff.

As outlined above, in some embodiments described herein above, the dilator 200 comprises varying regions of flexibility (i.e. rigid and flexible regions) to define a hybrid medical device. Since the dilator 200 comprises a fairly constant OD and ID and thus fairly constant wall thickness along its length, the behavior of the various regions, in terms of rigidity, is governed by the stiffness of the materials used. For example, the higher the stiffness of a material, the greater the rigidity, and the lower the stiffness of the material the lower the rigidity. Alternatively, in other embodiments, a single material may be used to form the dilator where the varying regions of flexibility are provided by varying the wall thickness along the respective regions. For example, an HDPE dilator may be provided with a relatively thin wall thickness along the flexible intermediate region and a relatively thicker wall thickness along the distal end region, in order to provide a dilator with the functionality described previously hereinabove.

The Sheath

Figure 3A:
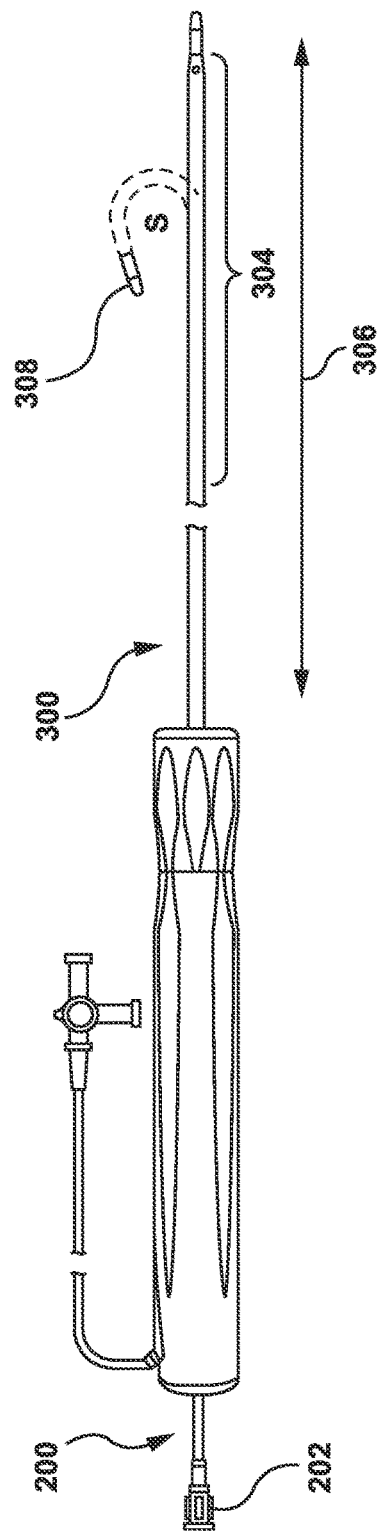
FIGS. 3A-3C illustrate a dilator in use with a steerable sheath, in accordance with various embodiments of the present invention.
Figure 3B:
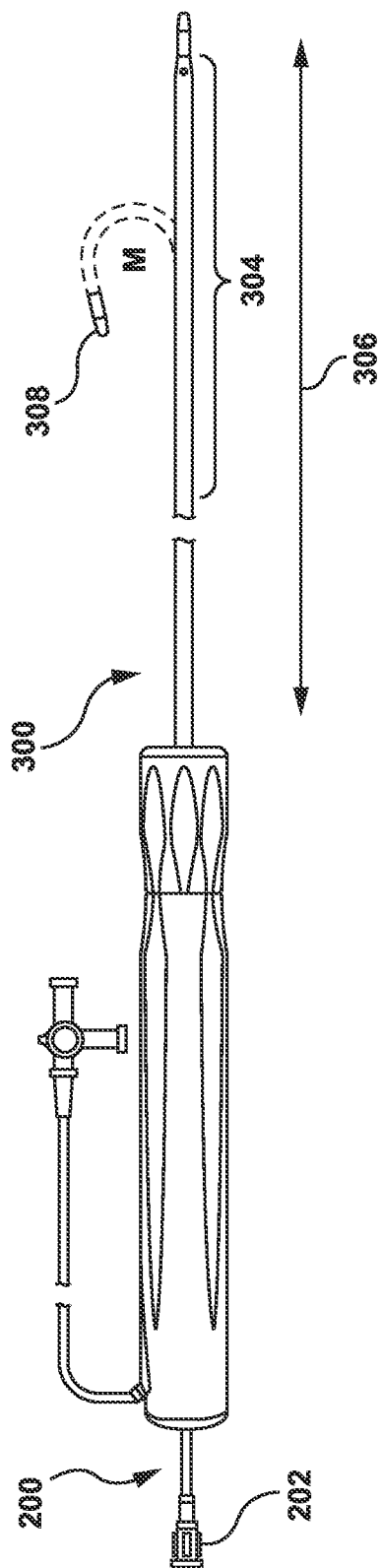
Figure 3C:
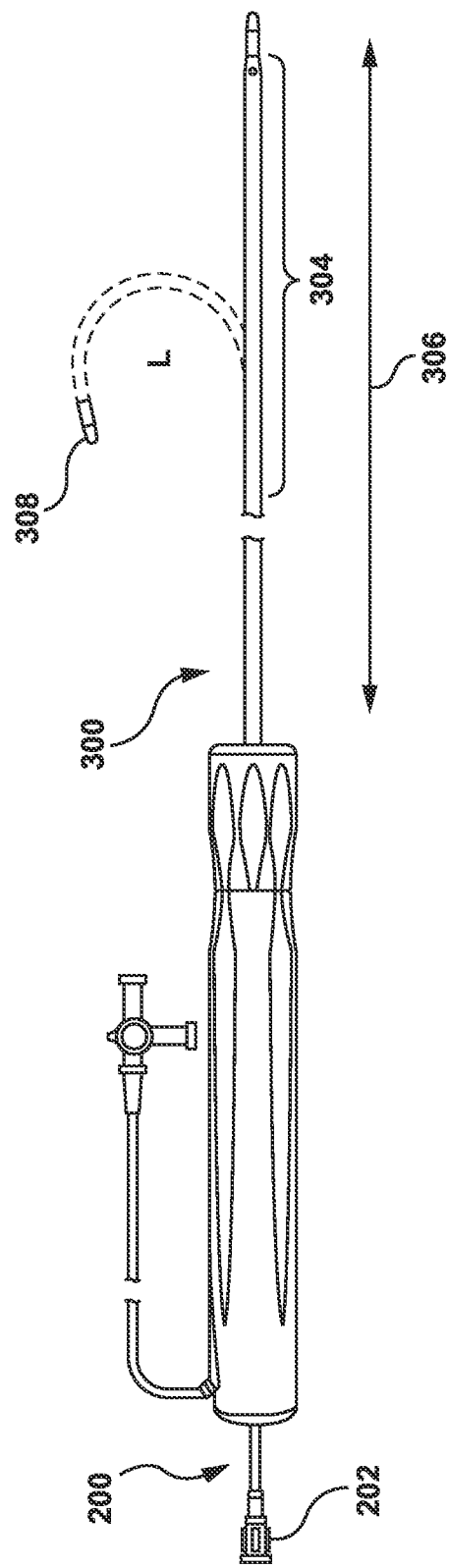

With reference now to FIGS. 3A-3C, various embodiments of a steerable sheath 300 are shown with the dilator 200 inserted there-through. In some embodiments, once the dilator 200 has been inserted through the steerable sheath 300, the dilator 200 extends by a distance, for example about 3 cm, distally beyond the distal end or tip of the steerable sheath 300 (more specifically, beyond the distal end/edge of the steerable sheath 300). In some embodiments, the dilator extends by between about 2 cm to about 4 cm beyond the distal edge of the steerable sheath 300. In some embodiments, the steerable sheath 300 has a usable length 306 that is between about 45 cm to about 71 cm.

In one specific example, with reference now to FIG. 3A, the steerable sheath 300 is an 8.5 French unidirectional steerable sheath, that has a deflectable region or articulating portion 304 operable to adopt a curve S having an angle of about 180 degrees and a having a radius of curvature of about 8.5 mm. Alternatively, in the example as shown in FIG. 3B, the deflectable region or articulating portion 304 of the steerable sheath 300 is operable to adopt a curve M having a radius of curvature of about 11 mm. In another example as shown in FIG. 3C, the deflectable region or articulating portion 304 of the steerable sheath 300 is operable to adopt a curve L, having a radius of curvature equal to about 25 mm.

In one particular embodiment, the dilator 200 is usable with an ancillary device such that it allows the ancillary device to maintain or reach its intended shape or curvature in order to access a desired tissue site within a region of tissue within a patient's body. The dilator 200 may be of the type described herein above, that comprises a rigid distal end region 206 and a flexible intermediate region 208 terminating at the distal end region 206, with the rigid distal end region 206 having a rigidity greater than the flexible intermediate region 208 to enable the dilator 200 to advance through tissue. The dilator 200 is configured for use in conjunction with the ancillary device such that during use, the flexible intermediate region 208 corresponds to a region of the ancillary device that is functional for imparting or providing a curvature. In one particular example, the dilator 200 is advanced over or through the ancillary device such that such that during use the flexible intermediate region 208 of the dilator 200 does not affect the region of the ancillary device that is functional for imparting a curvature, allowing the ancillary device to substantially maintain or reach its intended position or shape in order to position the dilator rigid distal end region 206 at a desired location within the region of tissue.

In one such example, the ancillary device comprises a steerable device such as a sheath, catheter or guidewire that is steerable, where the ancillary device is functional for imparting a curvature by actuation of the ancillary device. When in use in conjunction with the dilator 200, the flexible intermediate region 208 of the dilator does not inhibit or prevent the ancillary device from reaching its intended curvature upon actuation to position the dilator distal end region 206 at a desired location.

In alternative embodiments, a telescoping steerable sheath may be used in order to enhance target site-selection.

Alternatively, in some embodiments, the ancillary device comprises a fixed curve device such as a fixed curve sheath that has a preformed curve. Similar to embodiments discussed previously herein, the fixed curve sheath is usable with the dilator 200 and during use the flexible intermediate region 208 of the dilator 200 does not affect the preformed curvature of the sheath, thus allowing the sheath to position the rigid distal end 206 of the dilator 200 at the desired location within the region of tissue. Furthermore, the use of the dilator 200, in accordance with an embodiment of the present invention, may prevent the need for over curving the sheath in anticipation of a substantial decrease in curvature of the sheath once the dilator 200 there-through.

In some embodiments, it may be desirable to use a hybrid dilator comprising features that provide a dual functionality of a sheath and a dilator. The hybrid dilator provides the smoothness of a standard dilator with the control of a steerable sheath. More specifically, the hybrid dilator functions as a single device that removes the need for using conventional sheath/dilator assemblies and eliminates the need for an assembly, resulting in less waste, fewer exchanges, and reduced procedure times. The hybrid dilator may comprise a sheath-like handle with familiar torque and tactile control. For example, the hybrid dilator comprises a proximal portion of a sheath hub with an actuation mechanism to steer the distal portion. The shaft extending from the hub is similar to that of a dilator wherein the distal tip comprises a tapered portion which may be used to dilate the puncture.

In accordance with embodiments of the present invention, as described hereinabove, FIGS. 1A-1B, 2A-2C, and 3A-3C illustrate embodiments of a medical device operable to be guided to a tissue site to puncture tissue and to function as a rail for installing devices thereupon. Such embodiments provide efficiencies to medical procedures in which they are utilized as they perform multiple functions and thereby reduce the amount of device exchanges that need to be performed. The "hybrid" medical devices further facilitate the access and puncture of a tissue site upon insertion at a particular access site on a patient's body.

Figure 4:
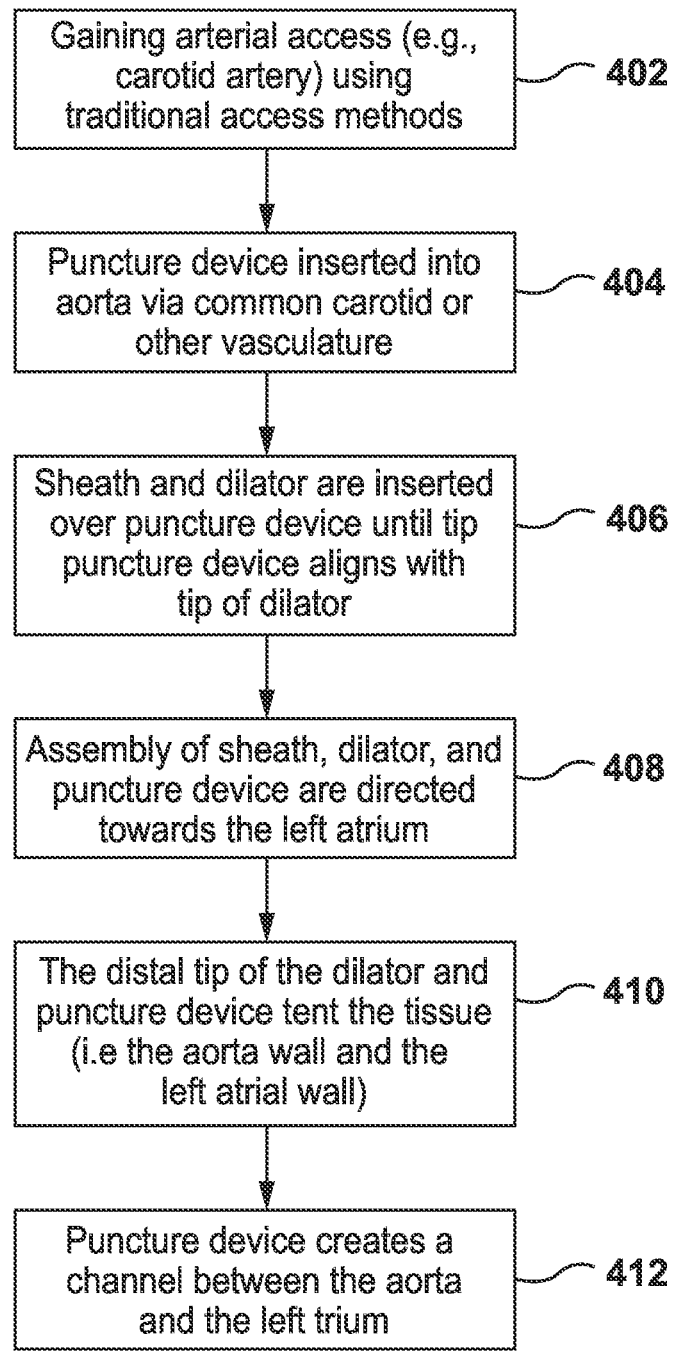
FIG. 4 illustrates a method of accessing the left atrium via the ascending aorta, in accordance with an embodiment of the present invention.

By way of example, the flowchart illustrated in FIG. 4 summarizes the method and device for superior access for the creation of fluid communication from the aorta to the left atrium. The method may comprise the steps of:

(i) Gaining arterial access using traditional access methods, such as the Seldinger technique 402. One example of arterial access may be accessing the carotid artery.

(ii) Once access is achieved, the puncture device (such as a radiofrequency guidewire) is advanced along the carotid artery and into the aorta 404. In an alternative embodiment, aorta access may be achieved through other vasculature (such as the left subclavian artery or the left common iliac artery).

(iii) The sheath (such as a steerable sheath) and dilator (such as a flexible dilator) are then inserted and advanced over the puncture device such that the tip of the puncture device aligns with the tip of the dilator 406.

(iv) The assembly is then positioned such that the tip of the assembly is directed, within the aorta, towards the left atrium 408. The user may use various anatomical landmarks to help direct the assembly, for example, the user may direct the assembly such that the distal tip is proximate the sinotubular junction (STJ) while the assembly is within the ascending aorta.

(v) Once the target position is achieved, the distal tip of the dilator and puncture device may be used to tent the tissue between the aorta and left atrial wall 410.

(vi) The puncture device may then be used to create a channel between the aorta and left atrium 412. For example, if using a radiofrequency guidewire for the puncture device, energy may be delivered from the distal tip of the guidewire to the tissue in order to form a puncture. In an alternative embodiment, a sharp tip puncture device may be used to mechanically create the puncture between the aorta and left atrial wall.

In some instances, the user may further advance the assembly into the left atrium. Upon advancement, the puncture between the aorta and left atrial wall may be enlarged to accommodate for larger end therapy devices.

The user may perform the additional step of externalizing the puncture device (for example a radiofrequency guidewire). This step involves tracking the radiofrequency guidewire from the left atrium to the inferior vena cava and exit via femoral vein access. This enables users to support the advancement of end-therapy devices from the femoral vein and into the left atrium. The exemplary method will be further explained in detail hereinbelow.

Figure 5A:
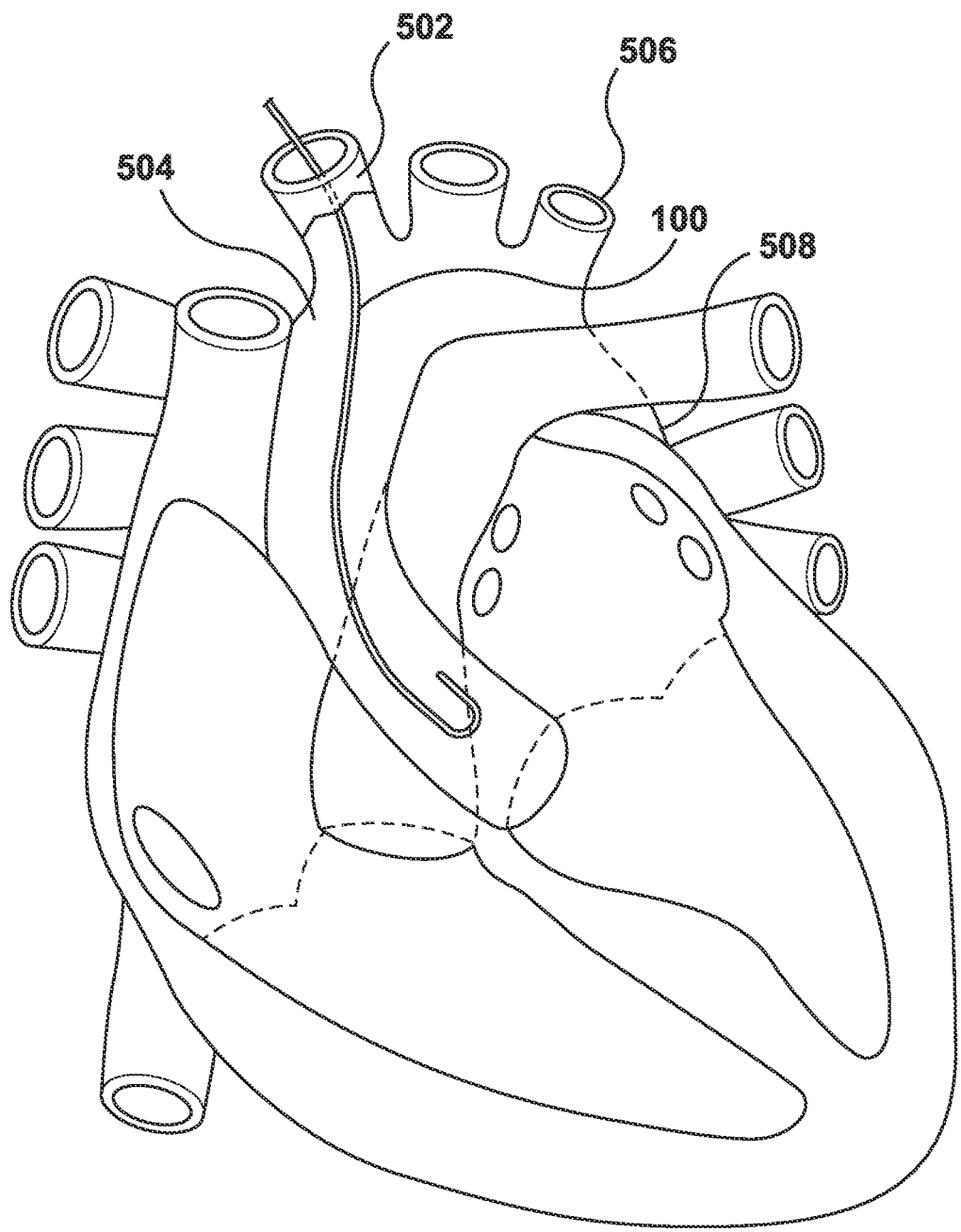
FIG. 5A-5D illustrates the steps of a method for accessing the left atrium via the ascending aorta, in accordance with an embodiment of the present invention.

Creating Fluid Communication Between the Aorta and Left Atrium via Superior Access Access to the vasculature for creation of the communication is achieved from a superior approach through the common carotid arteries. The common carotid arteries may be accessed using traditional access procedures, such as the Seldinger technique, with the placement of a hemostatic valve. A puncturing device 100 may then be inserted into a carotid artery which would provide the most direct path to the target puncture site in the aorta. In the following embodiments, the puncturing device 100 is illustrated as a flexible puncturing device 100, such as a flexible puncturing guidewire; however, the puncturing device 100 may be any alternative device used for puncturing tissue, such as a steerable needle, a steerable power catheter or a mechanical puncturing wire. For example, the right carotid artery 502 would provide a path to the ascending aorta 504 while the left carotid artery 506 would provide a path to the descending aorta 508. In an alternative example, the left carotid artery 506 may provide a pathway to the ascending aorta 504. The flexible puncturing device 100 is then advanced into the aorta. As an example, FIG. 5A illustrates the puncture device 100 being advanced from the right carotid artery 502 into the ascending aorta 504. However, in an alternative embodiment, the puncturing device 102 may be advanced from the left carotid artery 506 into the descending aorta 508. When puncturing from the descending aorta 508, the physician may be able to use the pulmonary veins as anatomical landmarks prior to tenting the tissue. Specifically, the physician may choose to target the site located between the left and right pulmonary veins.

Figure 5B:
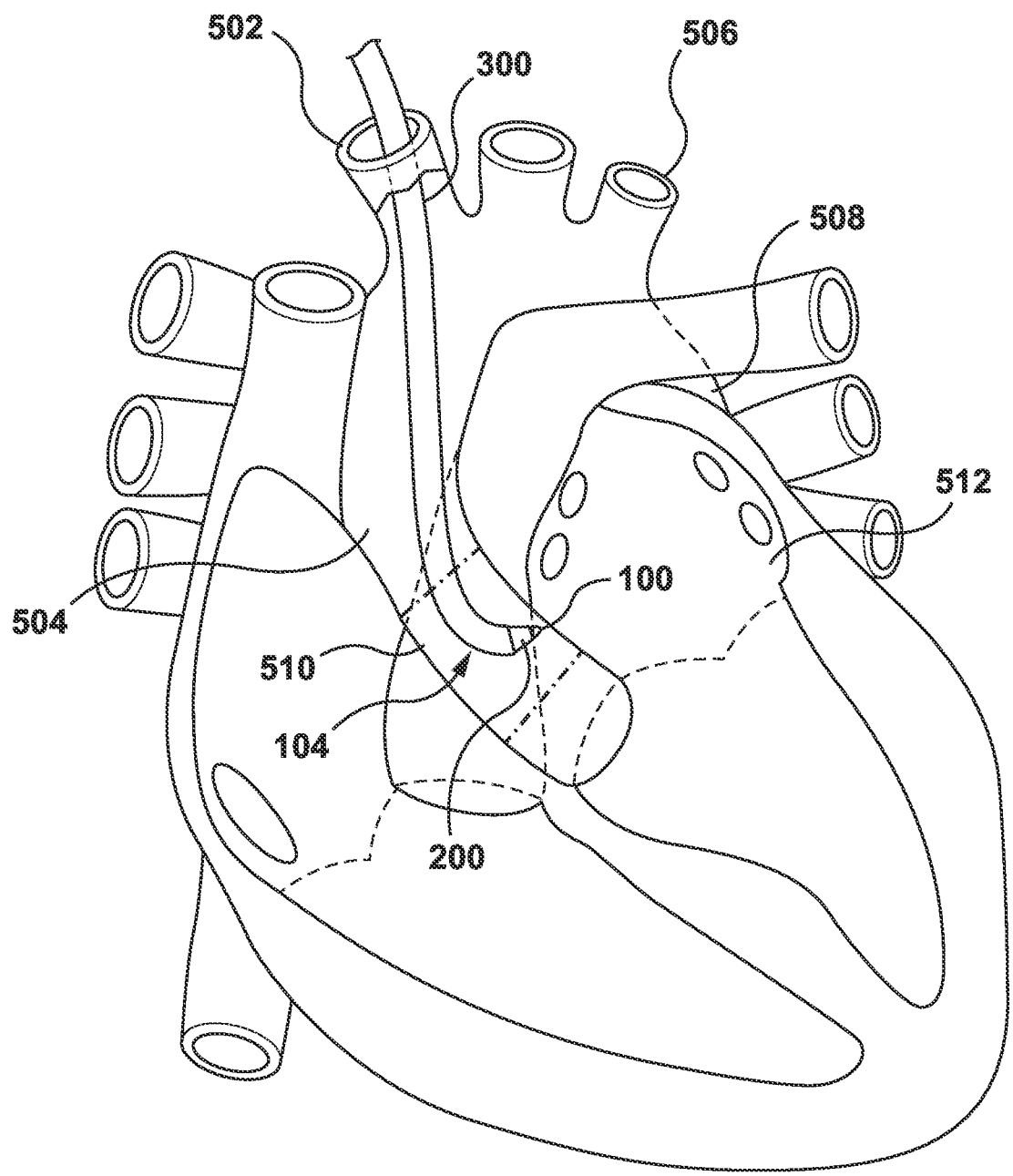

As illustrated in FIG. 5B, a sheath 300 (such as a steerable sheath, a fixed curve sheath, a small-bore steerable sheath <10 Fr, or a large-bore steerable sheath >15 Fr, or a telescoping steerable sheath) and dilator 200 (such as a flexible dilator) are inserted over the flexible puncturing device 100 until the distal tip of the flexible puncturing device 100 is aligned with the distal tip of the dilator 200. The assembly 104 of the sheath 300, dilator 200, and flexible puncturing device 100 are positioned within the aorta and directed to the puncturing target site. Support and etiology of surrounding vasculature may be used to determine an appropriate target site selection. Methods for selecting the appropriate target site are described further in this application. For example, the sinotubular junction (STJ) 510 may act as an anatomical landmark and aid in positioning the assembly 104 towards the left atrium 512 to create communication between the ascending aorta 504 and the left atrium 512. In this instance, the distal end of the assembly 104 may be positioned such that it is proximate the STJ. Alternatively, positioning the assembly between the left superior and inferior pulmonary veins may aid in creating communication between the descending aorta and the left atrium. This step can optionally be facilitated using fluoroscopy (e.g. in examples wherein the puncturing device 100 or the assembly 104 includes one or more radiopaque markers or features), angiography, electro-anatomical mapping (EAM) (e.g. to confirm real-time positioning of the puncturing tip of the puncturing device 100 using real-time or pre-determined computerized tomography data, in conjunction with a catheter or guidewire with one or more EAM markers in the aorta, intracardiac and/or transesophageal echocardiography (ICE and/or TEE) (e.g. using echogenic markers or features on the puncturing device 100 or on the sheath 300 and/or dilator 200).

Figure 5C:
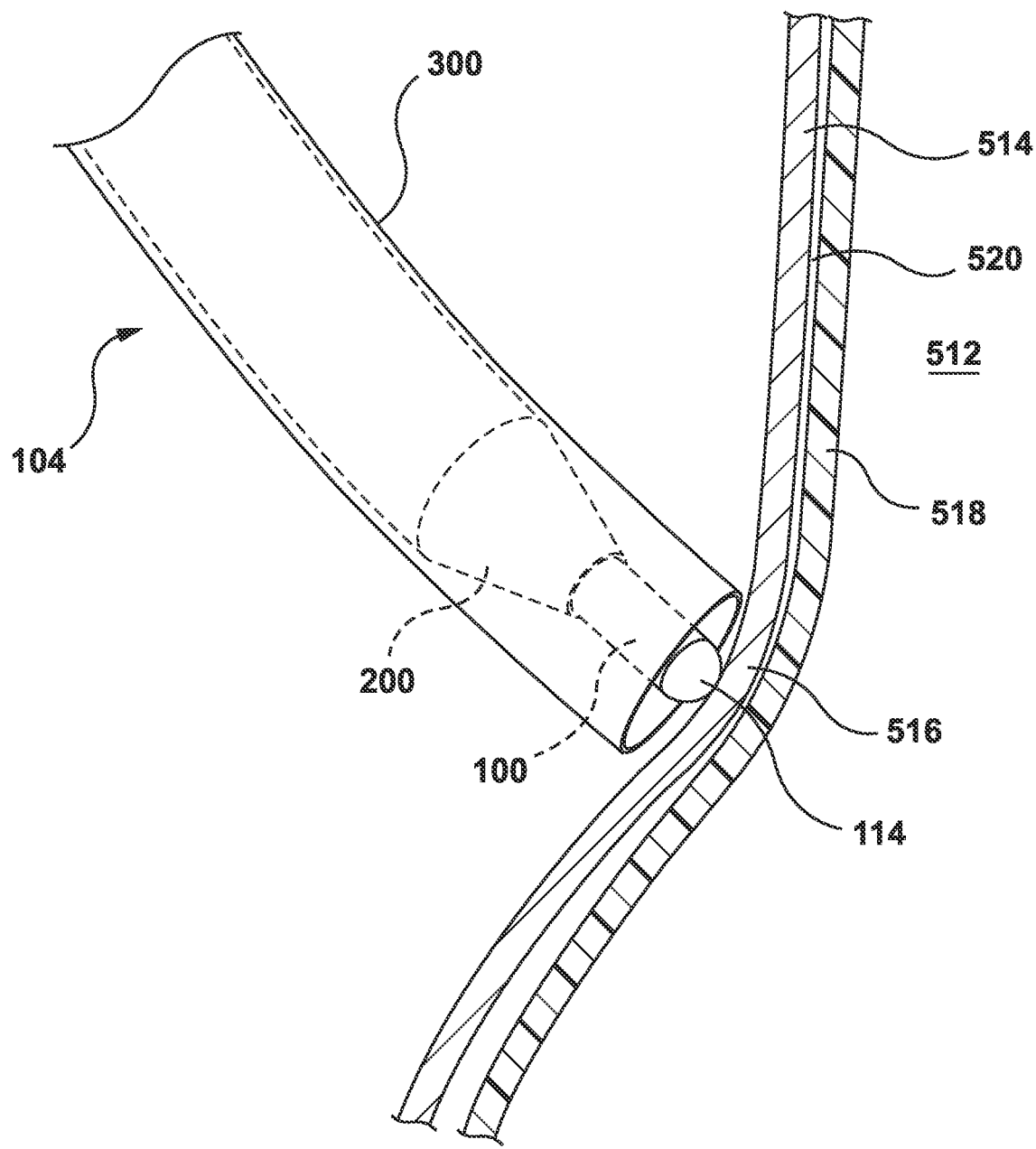

Once the assembly 104 is directed at the target puncturing site, the assembly 104 tents the tissue 516 between the aorta wall 514 and left atrium 512 (as seen in FIG. 5C). In some embodiments, the dilator 200 is retracted into the sheath 300, thereby enabling the sheath 300 to act as a stabilizer while positioning against the target tissue while enabling the dilator to provide support to the flexible puncturing device 100. This allows the forward force on the assembly 104 to be evenly distributed across the vessel (i.e., the aorta wall 514), decreasing the risk of inadvertent perforation of the tissue with the dilator or inadvertent dilation of the aorta wall 514 or left atrium wall 518. The prevention of inadvertent puncture/dilation is important to prevent blood from leaking into the transverse pericardial sinus 520. The transverse pericardial sinus 520 is a space between the aortal wall 514 and left atrium wall 518 and is within the pericardial cavity of the heart. As soon as a puncture is created and dilated, blood may leak into the transverse pericardial sinus 520. Ideally, a physician will create a puncture and wait until they are ready to apply a stent or end-therapy device before dilating between the two tissues.

Radiofrequency energy is then applied to the flexible puncturing device 100 and delivered to the tissue via the energy delivery device 114. The flexible puncturing device 100 is advanced during energy application, creating a puncture between the aorta and left atrium, forming a hole or pathway to allow fluid communication between the aorta and the left atrium. In an alternative embodiment, the puncturing device 100 may comprise a sharp distal tip which may be used to mechanically puncture the tissue.

Confirmation of access into the left atrium from the aorta may be achieved through various methods, including fluoroscopy, electro-anatomical mapping (EAM), pressure differentials between the aorta and left atrium, contrast injection, or using intracardiac echocardiography (ICE) or transesophageal echocardiography (TEE).

Figure 5D:
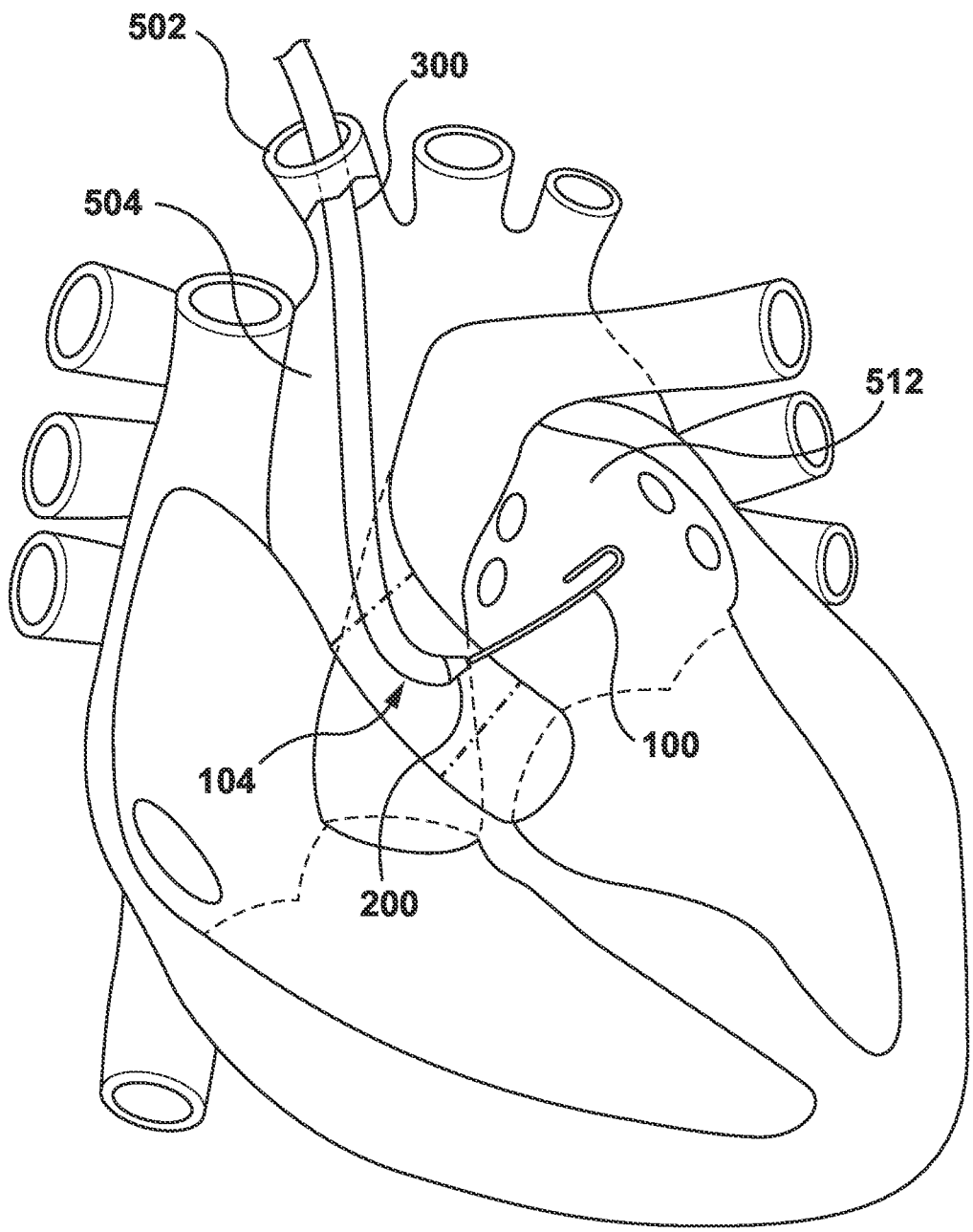

The dilator 200 may then be advanced, over the flexible puncturing device 100, through the puncture site to dilate the tissue and enlarge the puncture site. The sheath 300 and dilator 200 may then be removed, leaving the flexible puncturing device 100 within the left atrium 512 to act as a guiderail for advancing end-therapy devices into the left atrium 512, as illustrated in FIG. 5D. In some instances, the sheath may be advanced into the left atrium, overtop of the flexible puncturing device, if the access sheath is able to support the delivery of the end-therapy devices.

Optimal Puncturing Target Site Selection Using Various Visualization Methods

Optimal target selection for puncture from the aorta into the left atrium 512 may be determined using various visualization methods. One method may utilize fluoroscopy, which creates images in real time to provide guidance. Radiopaque markers may be placed on the ancillary devices, such as the sheath 300 or dilator 200, and the flexible puncturing device 100 to provide physicians with indicators as to the location of the devices throughout the procedure.

Figure 6:
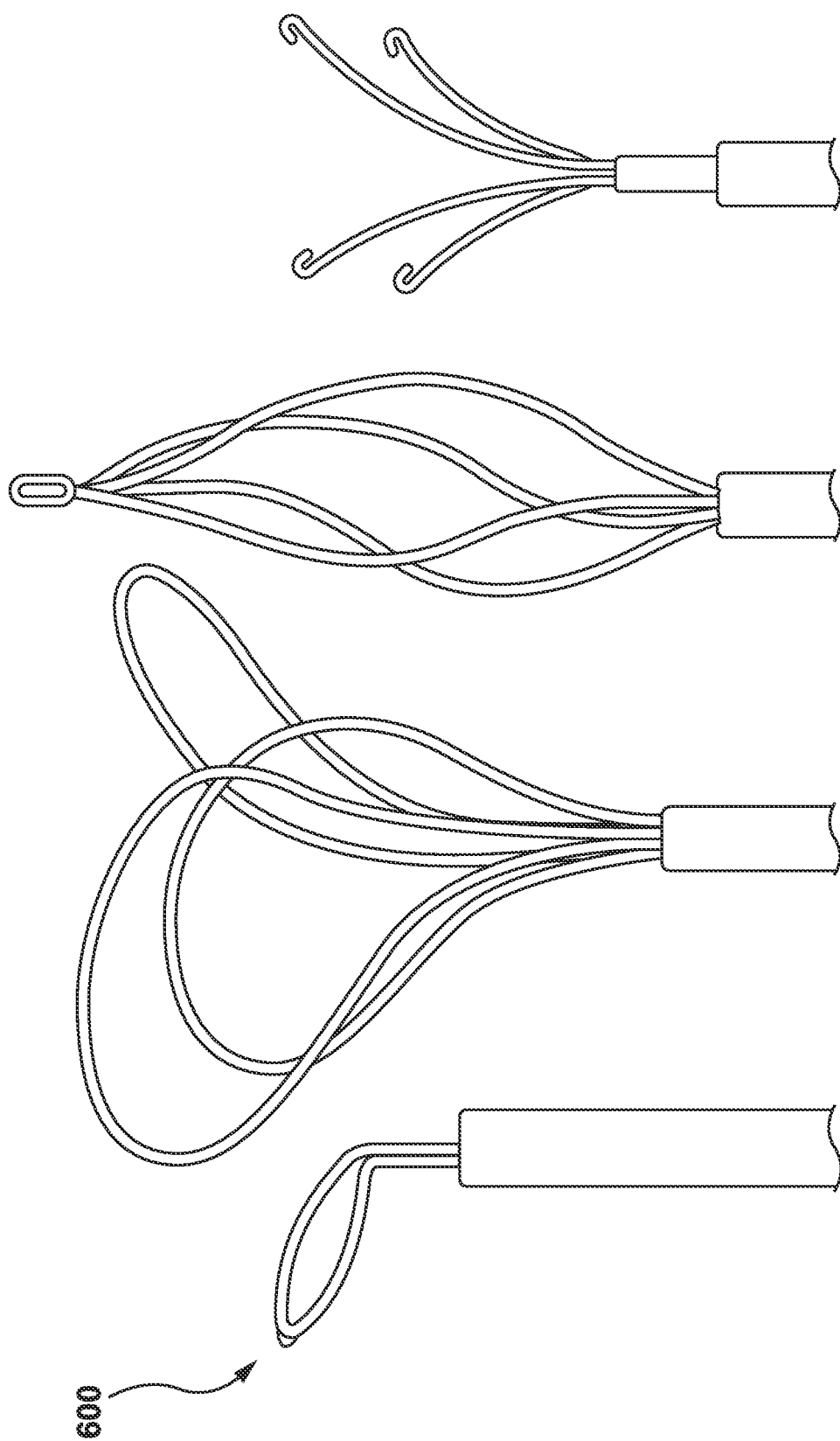
FIG. 6 illustrates an example of a lasso catheter, in accordance with an embodiment of the present invention.

Alternatively, fluoro-less visualization techniques may be used. For example, electro-anatomical mapping (EAM) may provide the physician with real-time placement of the flexible puncturing device 100 and ancillary devices (such as sheath 300 and dilator 200) to targets. The puncturing targets may be pre-determined from a computed topography (CT) scan or, alternatively, may be determined in real-time. In real-time, a catheter or guidewire with one or more electro-anatomical mapping markers, such as a lasso catheter 600 (some examples can be seen in FIG. 6), may be placed in the left atrium to provide physicians with a target. Another method may use echogenic markers or features on the flexible puncturing device and ancillary devices may enable physicians to utilize ICE or TEE to determine the optimal target site.

Externalizing the Puncturing Device

In some instances, physicians may require the flexible puncturing device 100 to be externalized in order to support the advancement of end-therapy devices. A common access site for advancement of end-therapy devices is the femoral vein; in other words, a physician may want to externalize the flexible puncturing device 100 through the femoral vein. By externalizing the flexible puncturing device 100 the surgeon is able to secure one or both ends of the flexible puncturing device 100 to create a stiff guiderail for advancing end therapy devices.

Figure 7A:
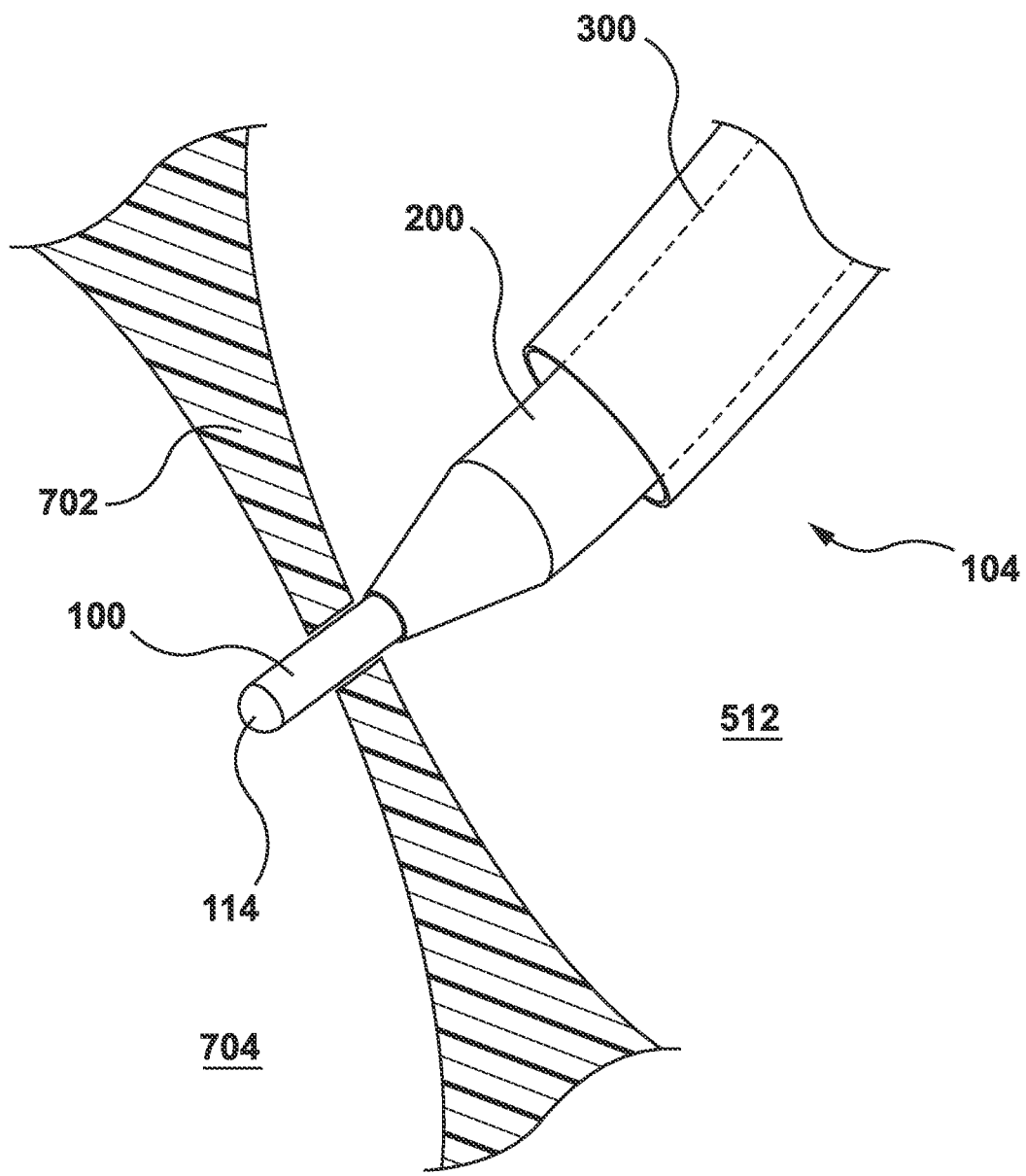
FIG. 7A-7D illustrates the steps of a method for externalizing the puncture device, in accordance with an embodiment of the present invention.
Figure 7B:
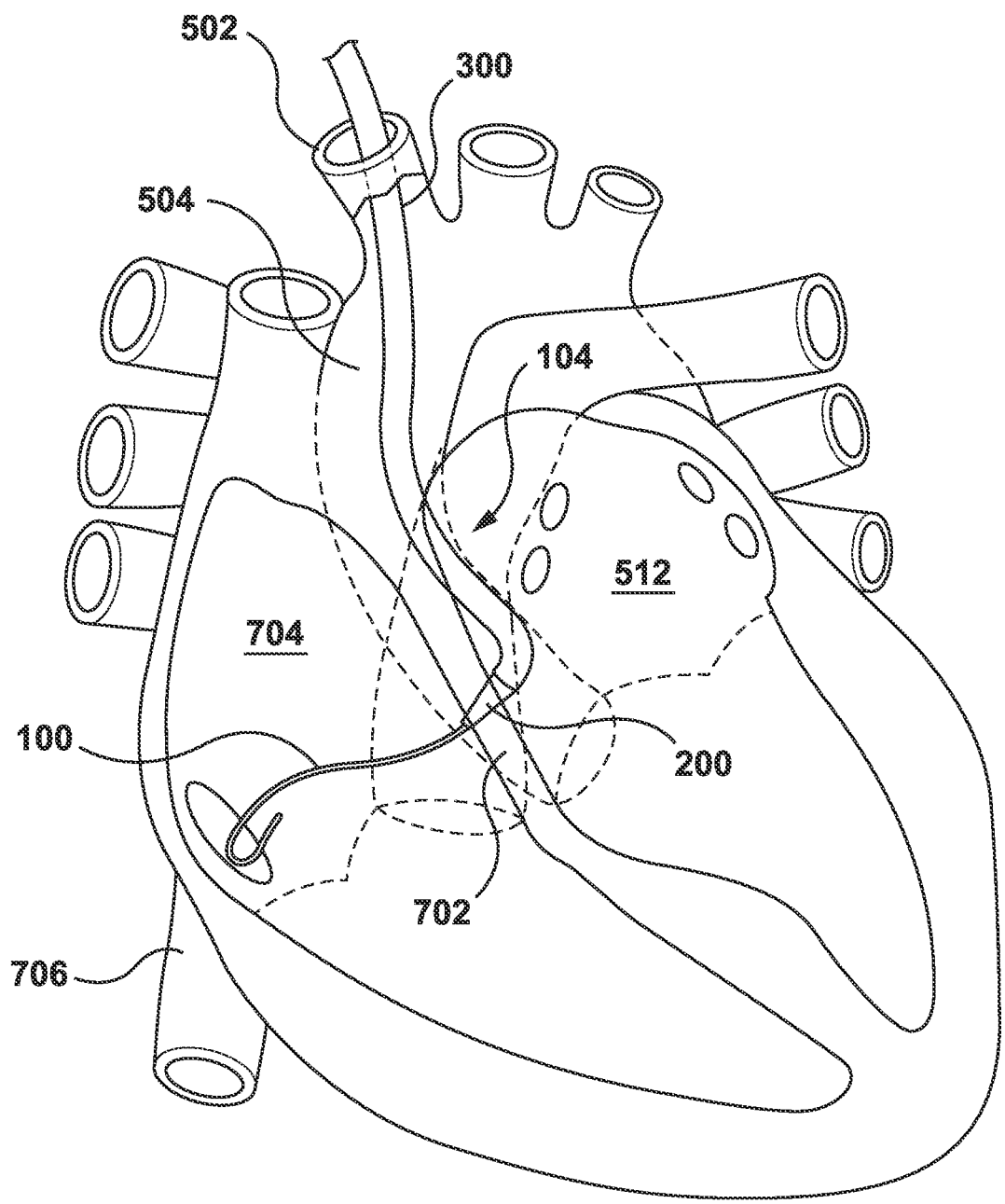
Figure 7C:
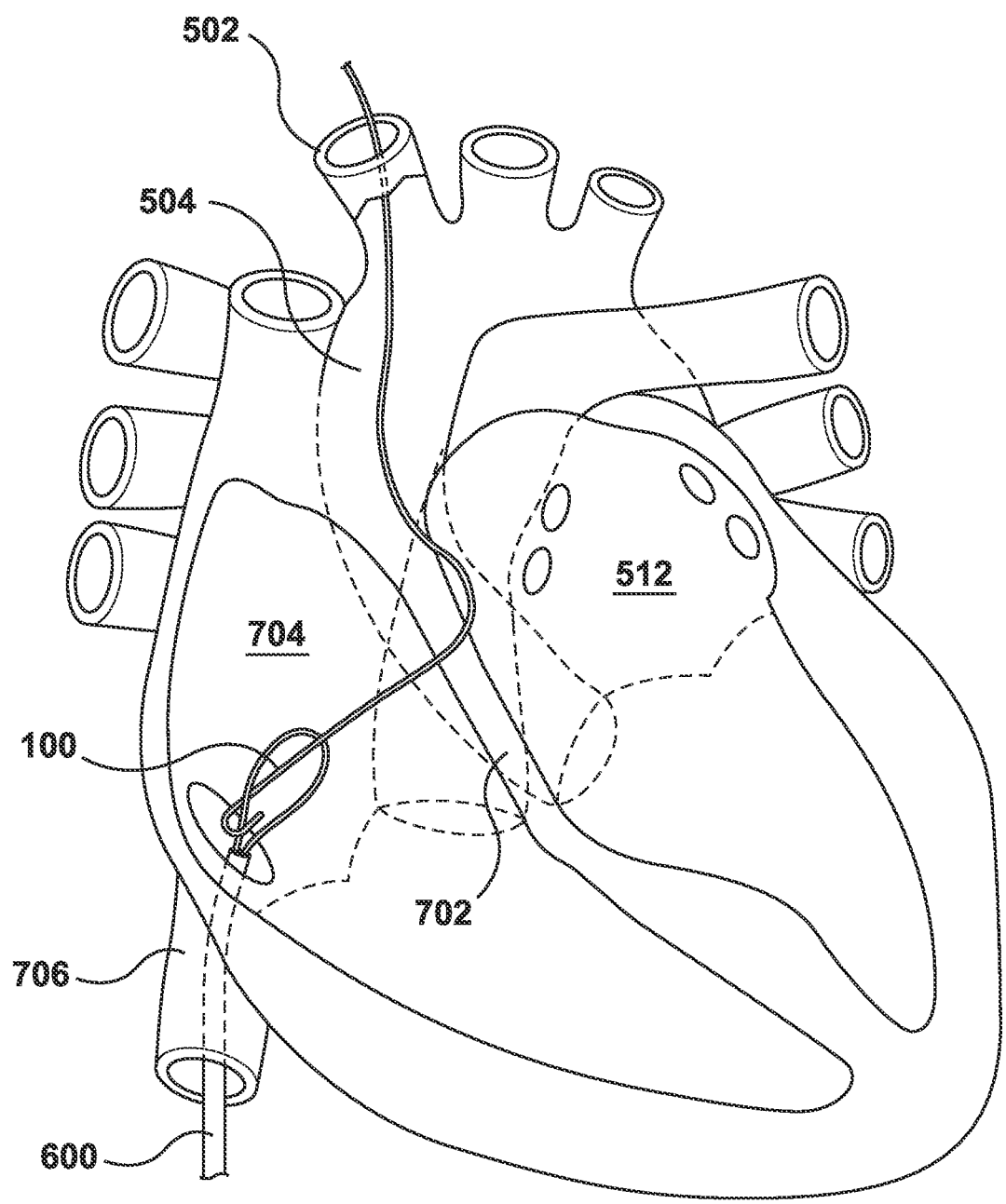
Figure 7D:
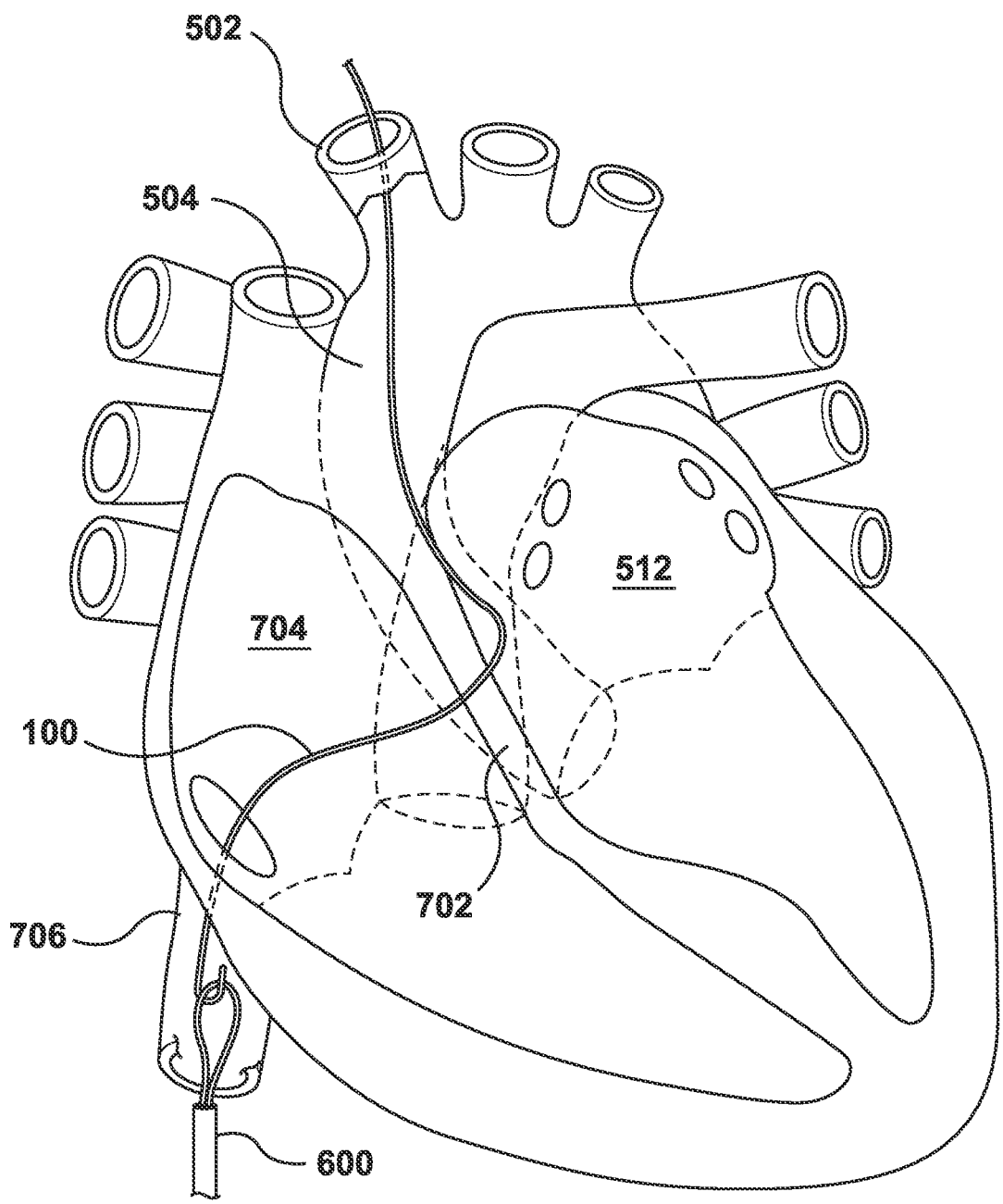

In this embodiment, after confirming access into the left atrium 512 from a superior approach as described above (and illustrated in FIGS. 5A to 5D), the sheath 300 and dilator 200 would be advanced into the left atrium 512. The flexible puncturing device 100 is then retracted to align with the dilator 200 tip, in preparation for a secondary puncture. The sheath 300 may then be maneuvered (i.e., steered) such that it is directed to the interatrial septum 702. Once in position, the assembly 104 tents the tissue and energy is delivered to the flexible puncturing device 100. As energy is delivered from the energy delivery device 114 of the puncturing device 100 to the tissue, the flexible puncturing device 100 is advanced, creating a puncture in the interatrial septum 702, as shown in FIG. 7A. In an alternative embodiment, the flexible puncturing device 100 may comprise a sharp distal tip which may be used to mechanically puncture the interatrial septum. As illustrated in FIG. 7B, the flexible puncturing device 100 may then be advanced from the left atrium 512 into the right atrium 704. At this point, the sheath 300 and dilator 200 may be optionally withdrawn, leaving the flexible puncturing device 100 in the right atrium 704. In one embodiment, a lasso catheter 600 may be advanced up the inferior vena cava and positioned in the right atrium 704. The lasso catheter 600 may act as a target to snare or capture the puncture device 100 once entering the right atrium 704 (FIG. 7C). Using the lasso catheter 600, the distal end of the flexible puncturing device 100 may be captured and tracked down the inferior vena cava 706 (FIG. 7D) into the femoral vein and out of a femoral venous access site. In this embodiment, the puncture device 100 would be dimensioned such that while the puncture device 100 is still accessible from the superior entry point, it is also externalized via the femoral vein. Alternatively, the lasso catheter 600 may be positioned within the inferior vena cava 706, and the puncture device 100 may be advanced and captured within the inferior vena cava 706, and from there the system may be externalized via the femoral vein. By allowing both ends of the puncture device 100 to be simultaneously secured by the user, the puncture device 100 may act as a stiff support track allowing advancement of end-therapy devices through the femoral access.

This process may be used if the end-therapy devices do not fit in the arterial vasculature. In one particular example, to facilitate large-bore access into the puncture between the left atrium and aorta, a large-bore access dilator and end-therapy sheath may be tracked over the flexible puncturing device via the femoral vein access. In this embodiment, the access sheath remains in the left atrium after the flexible puncturing device has been advanced through the right atrium, inferior vena cava, and exited out through the femoral vein access. As the large-bore access dilator and end-therapy sheath is brought into the left atrium, the large-bore access dilator can abut against the access sheath tip. The end-therapy sheath may then be advanced through the puncture between the left atrium and aorta, at the same time, the access sheath is retracted. Thus, the hemostasis of the left atrium to aortic communication into the pericardial space can be kept during the dilation.

Alternative Method for Externalizing the Puncture Device

Alternatively, the method of externalizing the puncture device 100 may involve positioning a snare, such as a lasso catheter 600, in the left atrium to capture the puncture device 100 once it enters the left atrium 512 from the aorta 504.

This method would involve gaining access to the left atrium 512 such that a lasso catheter 600 may be positioned within the left atrium 512. The lasso catheter 600 may act as a landing target for the flexible puncturing device 100 once it enters the left atrium 512 via the aorta 504. In one embodiment, the lasso catheter 600 may gain access to the left atrium 512 via a standard transseptal kit and procedure. For example, a physician may first gain access to the femoral vein wherein a guidewire is inserted and advanced into the right atrium via the inferior vena cava. The guidewire may be anchored within the heart (e.g., in the superior vena cava) such that it may then act as a rail for the delivery of the transseptal assembly (i.e., a transseptal needle, dilator, and sheath) which may be used to cross the septum. Alternatively, a puncturing guidewire (e.g., using radiofrequency energy or mechanical force) may be used instead of a standard guidewire. Using the transseptal assembly, the physician can gain access from the right atrium into the left atrium. The physician may remove the transseptal devices and advance a lasso catheter into the left atrium.

Figure 8A:
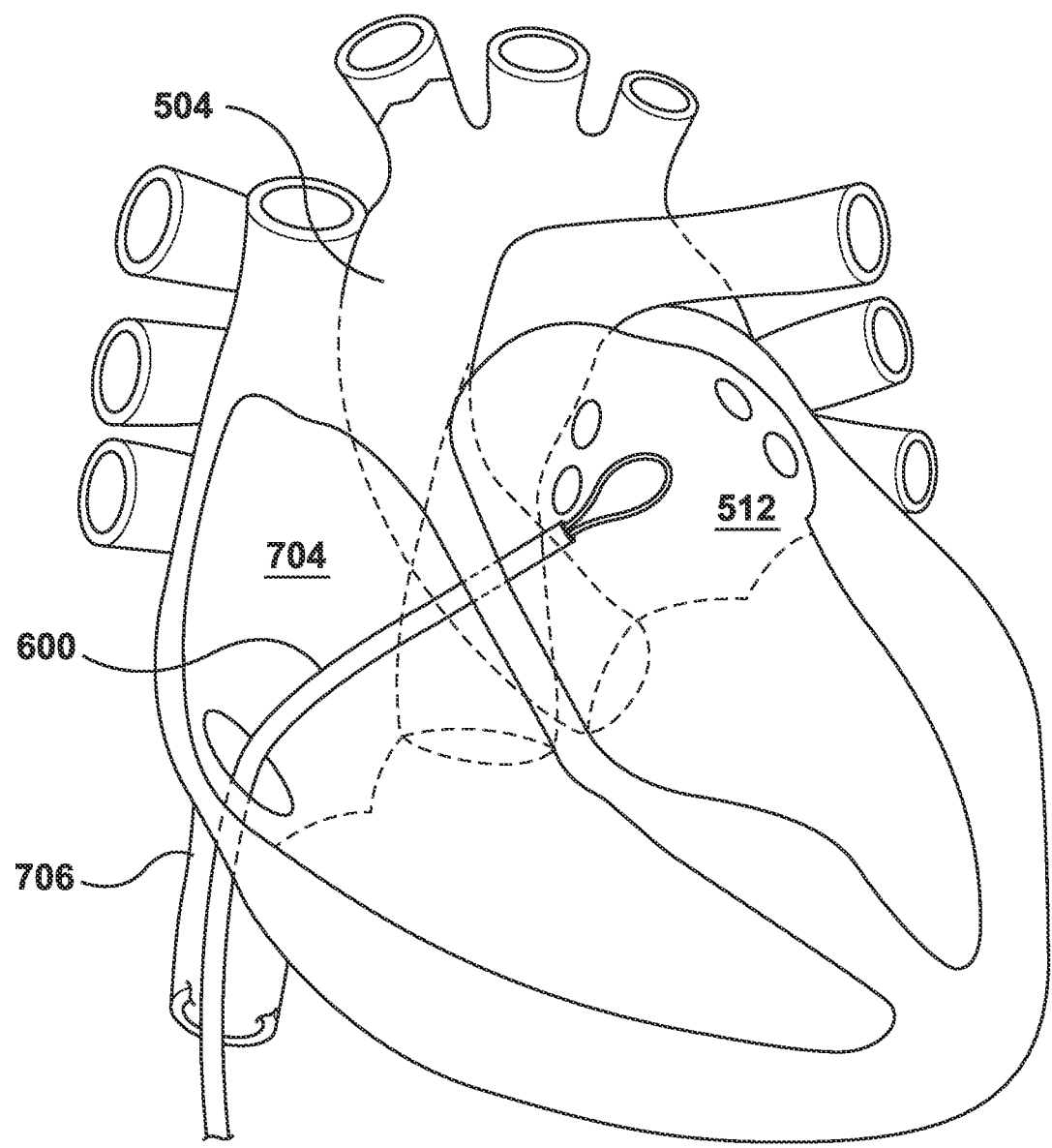
FIG. 8A-8D illustrates the steps of an alternative method for externalizing the puncture device in accordance with an alternative embodiment of the present invention.

With reference now to FIG. 8A, the lasso catheter 600 has been advanced into the left atrium 512. Preferably, this step may occur before the flexible puncture device 100, sheath 300 and dilator 200 have been advanced into the ascending aorta 504 (as depicted in FIGS. 5A and 5B), thereby allowing the lasso catheter 600 to aid in positioning by acting as a "landing zone" within the left atrium 512. Alternatively, the lasso catheter 600 may be advanced into the left atrium 512 after the assembly 104 has entered the ascending aorta 504. The lasso catheter 600 provides the physician with a target, for example acting as a snare, for when the puncturing device 100 enters the left atrium 512 from the aorta 504.

Figure 8B:
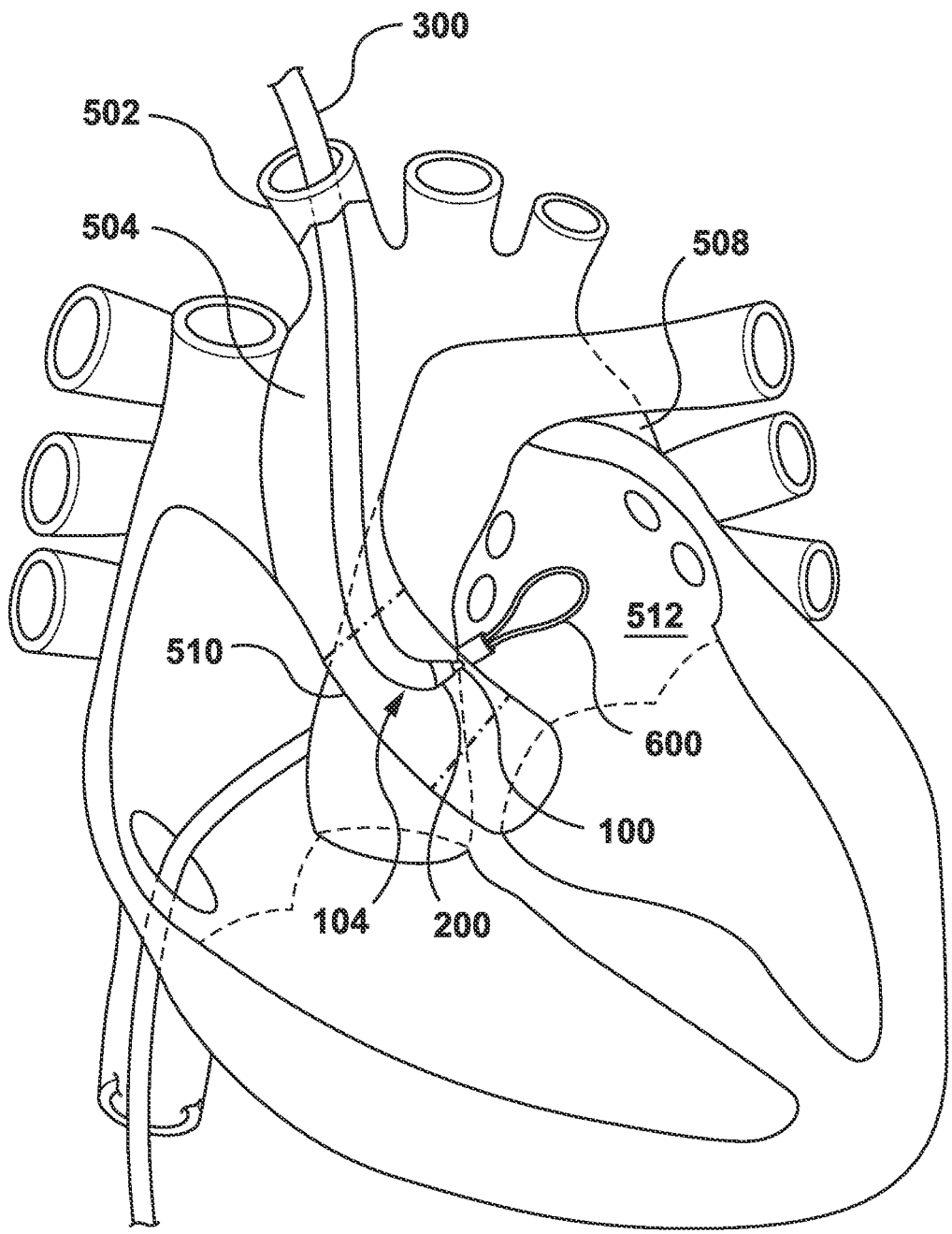

Similar to what was previously described above, the distal tip of the assembly 104 may be directed towards the left atrium 512. In some embodiments, this may be achieved by manipulating the steerable sheath 300 of the assembly 104, optionally using the STJ 510 of the ascending aorta 504 as an aid, the distal tip may be positioned towards the left atrium 512 (as seen in FIG. 8B). Once the assembly 104 is in position, the distal tip may be used to tent the tissue between the aorta wall 514 and left atrium 512, this step has been previously described and can be seen in FIG. 5C. Radiofrequency energy is then applied to the flexible puncturing device 100 and delivered to the tissue via the energy delivery device 114. While energy is being delivered, the flexible puncture device 100 may be advanced, thus creating a puncture between the aorta 504 and left atrium 512.

Figure 8C:
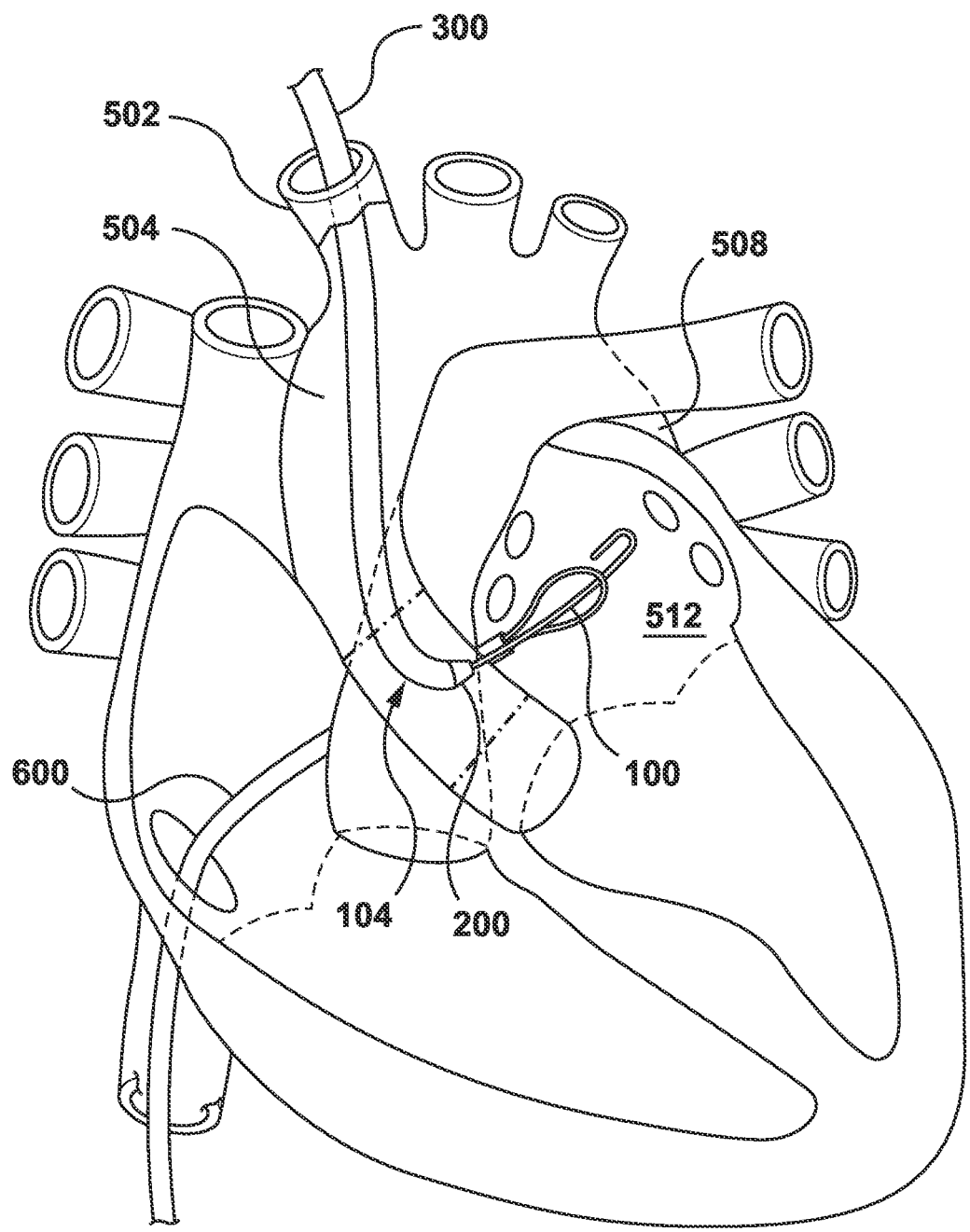
Figure 8D:
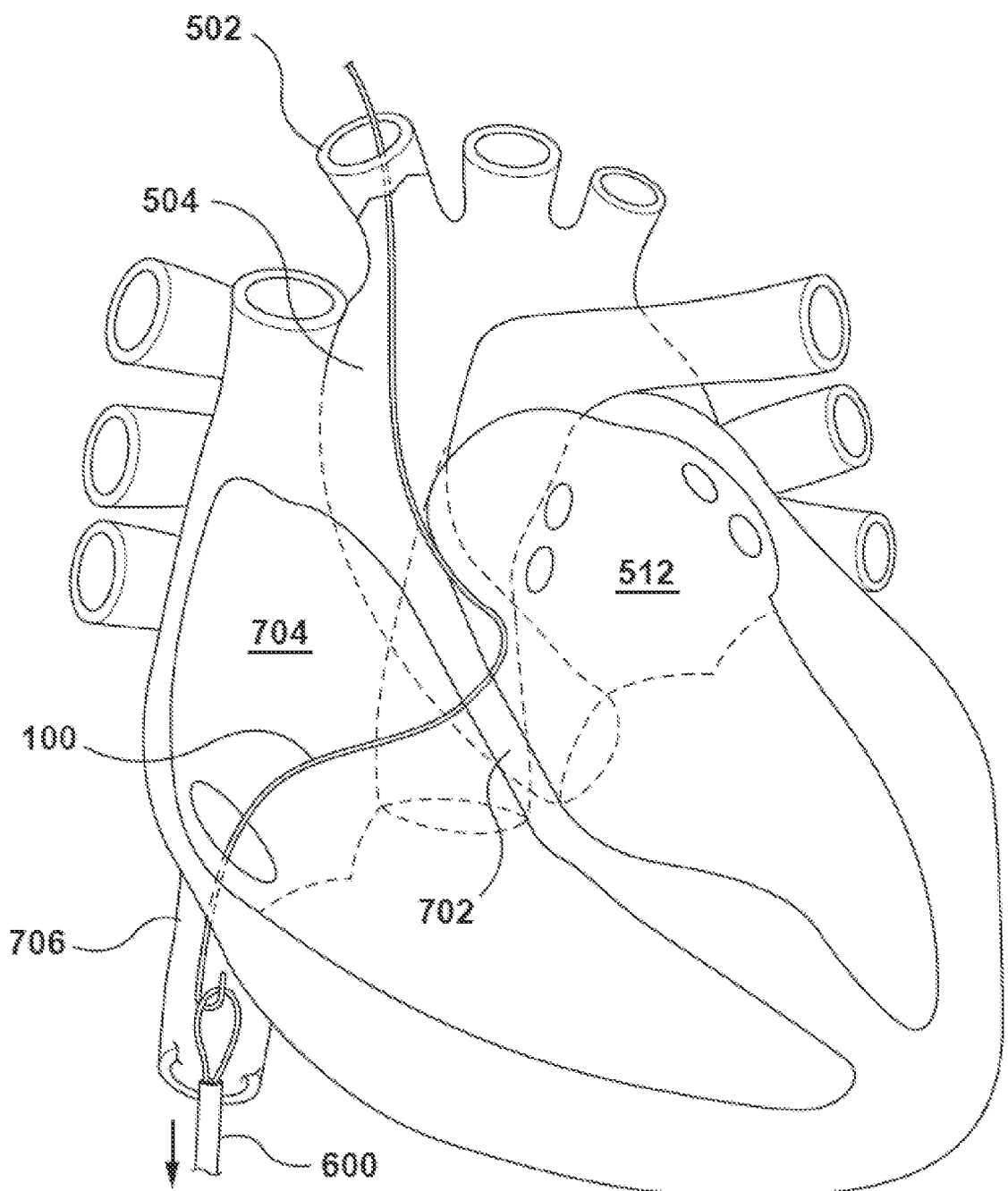

Upon being advanced into the left atrium 512, the snare (in this example the lasso catheter 600) captures the puncture device 100, as illustrated in FIG. 8C. At this point, the lasso catheter 600 may retract back towards the right atrium 704, pulling the puncture device 100 along with it. At this point, the sheath 300 and dilator 200 may optionally be withdrawn. The lasso catheter 600 may at this point continue to be retracted, bringing the flexible puncture device 100 from the right atrium 704 into the inferior vena cava 706 (seen in FIG. 8D) and externalizing at the femoral access at which the lasso catheter 600 had entered, thereby externalizing the puncture device 100. The puncture device 100 may then be used as a stiff guiderail for the delivery of end therapy devices. By allowing both ends of the puncture device to be simultaneously secured by the user, the puncture device may act as a stiff support track allowing advancement of end-therapy devices through the femoral access.

The embodiment(s) of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A method of puncturing, the method comprising the steps of:
   a. accessing a carotid artery and advancing a puncturing device through the carotid artery into an aorta;
   b. advancing a sheath and a dilator over the puncturing device through the carotid artery and into the aorta such that a puncturing tip of the puncturing device is aligned with a distal tip of the sheath and a distal tip of the dilator, forming a puncturing assembly;
   c. positioning the puncturing assembly at a target site within the aorta to gain access to a left atrium of a heart;
   d. tenting a tissue between the aorta and the left atrium using the puncturing assembly;
   e. creating a puncture through the tissue by advancing the puncturing device such that a channel between the aorta and the left atrium is formed;
   f. advancing an ensnaring device having one or more electro-anatomical mapping markers through an inferior vena cava into a right atrium to act as a target for the puncturing assembly;
   g. advancing the puncturing device into the left atrium from the aorta;
   h. advancing the sheath and the dilator over the puncturing device, through the puncture into the left atrium;
   i. positioning, using the ensnaring device as a target, the puncturing assembly at a position on an interatrial septum;
   j. tenting the interatrial septum using the puncturing assembly;
   k. creating a puncture through the interatrial septum by advancing the puncturing device;
   l. advancing the puncturing device through the interatrial septum and into a right atrium of a heart; and
   m. capturing and pulling the puncturing device, via the ensnaring device, through the inferior vena cava and into a femoral vein where it is exited from an access site.

2. The method of claim 1, wherein the puncturing device is a radiofrequency puncture device, the puncturing tip comprises an electrode to deliver radiofrequency energy, and step e. comprises delivering radiofrequency energy from the electrode while advancing the puncturing tip.

3. The method of claim 1, wherein the puncturing device is a mechanical puncture device, the puncturing tip comprises a sharp distal tip.

4. The method of claim 1, wherein the sheath is selected from a steerable sheath, a fixed curve sheath, a large-bore steerable sheath, or a telescoping steerable sheath, and the dilator is a flexible dilator.

5. The method of claim 1, further comprising a step of confirming creation of the channel with at least one of fluoroscopy, electro-anatomical mapping, pressure measurement, contrast injection, and echocardiography.

6. The method of claim 1, further comprising a step of advancing the dilator through the puncture, wherein the distal tip of the dilator comprises a dilating tip, thereby dilating the puncture upon advancement.

7. The method of claim 1, further comprising the step of securing at least one end of the puncturing device such that the puncturing device may be used as a stiff guiderail for advancing an end therapy device.

8. The method of claim 7, further comprising the step of advancing and delivering the end therapy device.

9. The method of claim 1, wherein the step of capturing and pulling the puncturing device is achieved by using a lasso catheter as the ensnaring device.

10. The method of claim 1, wherein the step of creating the puncture is performed by advancing a sharp tip of the distal tip of the puncturing device forward into the tissue.

11. The method of claim 1, wherein positioning the distal tip of the puncturing assembly comprises aligning the distal tip of the puncturing assembly with a sinotubular junction.

12. The method of claim 1, wherein the puncturing device includes an outer diameter of 0.035" or 0.032", and the dilator includes a flexible region that corresponds to a region of the sheath that is amenable to deflection.

13. A method of puncturing, the method comprising the steps of:
   a. accessing a carotid artery and advancing a puncturing device through the carotid artery into an aorta, wherein the puncturing device includes a distal portion having a pigtail or J-tip;

b. advancing a sheath and a dilator over the puncturing device through the carotid artery and into the aorta such that a puncturing tip of the puncturing device is aligned with a distal tip of the sheath and a distal tip of the dilator, forming a puncturing assembly;

c. positioning the puncturing assembly at a sinotubular junction within the aorta to gain access to a left atrium of a heart;

d. tenting tissue between the aorta and the left atrium at the sinotubular junction using the puncturing assembly;

e. creating a puncture through the tissue by advancing the puncturing device such that a channel between the aorta and the left atrium is formed;

f. advancing an ensnaring device having one or more electro-anatomical mapping markers through an inferior vena cava into a right atrium to act as a target for the puncturing assembly;

g. advancing the puncturing device into the left atrium from the aorta;

h. advancing the sheath and the dilator over the puncturing device, through the puncture into the left atrium;

i. positioning, using the ensnaring device as a target, the puncturing assembly at a position on an interatrial septum;

j. tenting the interatrial septum using the puncturing assembly;

k. creating a puncture through the interatrial septum by advancing the puncturing device;

l. advancing the puncturing device through the interatrial septum and into a right atrium of a heart; and m. capturing and pulling the puncturing device, via the ensnaring device, through the inferior vena cava and into a femoral vein where it is exited from an access site.

14. The method of claim 13, wherein the puncturing device is a radiofrequency puncture device, the puncturing tip comprises an electrode to deliver radiofrequency energy, and step e. comprises delivering radiofrequency energy from the electrode while advancing the puncturing tip.

15. The method of claim 13, wherein the puncturing device is a mechanical puncture device, the puncturing tip comprises a sharp distal tip.

16. The method of claim 13, wherein the puncturing device includes an outer diameter of 0.035" or 0.032", and the dilator includes a flexible region that corresponds to a region of the sheath that is amenable to deflection.

17. The method of claim 13, further comprising a step of advancing the dilator through the puncture, wherein the distal tip of the dilator comprises a dilating tip, thereby dilating the puncture upon advancement.

18. The method of claim 13, further comprising the step of securing at least one end of the puncturing device such that the puncturing device may be used as a stiff guiderail for advancing an end therapy device.

19. The method of claim 13, further comprising the step of advancing and delivering the end therapy device.

20. The method of claim 13, wherein the step of capturing and pulling the puncturing device is achieved by using a lasso catheter as the ensnaring device.

* * * * *